(12) United States Patent
Nason et al.

(10) Patent No.: US 12,137,895 B2
(45) Date of Patent: *Nov. 12, 2024

(54) ANCHORS AND METHODS FOR SECURING SUTURE TO BONE

(71) Applicant: CAYENNE MEDICAL, INC., Scottsdale, AZ (US)

(72) Inventors: Kevin S. Nason, Chandler, AZ (US); Jordan A. Hoof, Phoenix, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/112,903

(22) Filed: Feb. 22, 2023

(65) Prior Publication Data
US 2023/0200801 A1  Jun. 29, 2023

Related U.S. Application Data

(63) Continuation of application No. 16/269,215, filed on Feb. 6, 2019, now Pat. No. 11,612,387, which is a
(Continued)

(51) Int. Cl.
*A61B 17/04* (2006.01)
*A61B 90/00* (2016.01)

(52) U.S. Cl.
CPC ...... *A61B 17/0401* (2013.01); *A61B 17/0485* (2013.01); *A61B 2017/0409* (2013.01);
(Continued)

(58) Field of Classification Search
CPC ........ A61B 17/0401; A61B 2017/0409; A61B 2017/0412; A61B 2017/0414;
(Continued)

(56) References Cited

U.S. PATENT DOCUMENTS 5,486,197 A   1/1996  Le et al.
5,601,557 A   2/1997  Hayhurst
(Continued)

FOREIGN PATENT DOCUMENTS

EP   1825817 A1   8/2007
EP   1857054 A2   11/2007
(Continued)

OTHER PUBLICATIONS

U.S. Appl. No. 12/347,831 U.S. Pat. No. 9,295,460, filed Dec. 31, 2008, Anchors and Method for Securing Suture to Bone.
(Continued)

*Primary Examiner* — Todd J Scherbel
(74) *Attorney, Agent, or Firm* — SCHWEGMAN LUNDBERG & WOESSNER, P.A.

(57) ABSTRACT

A method for securing suture to bone comprises drilling a hole in a desired portion of bone at a desired procedural site, passing a strand of suture through a portion of soft tissue to be approximated to the portion of bone, and extending the free suture ends proximally from the soft tissue. The suture is loaded into an anchor implant. Using an inserter, on a distal end of which is attached the anchor implant, the anchor implant is manipulated into the bone hole. The suture is then tensioned to a desired level by pulling on the free suture ends, after the anchor implant is positioned in the bone hole. The free suture ends are wrapped about a suture cleat on an inserter handle once the desired tension level is achieved. A proximal anchor component is moved distally to engage with a distal anchor component to lock the anchor in place within the bone hole, and to lock the suture in place within the anchor. Then, the inserter is removed from the procedural site.

20 Claims, 18 Drawing Sheets

Related U.S. Application Data continuation of application No. 15/046,414, filed on Feb. 17, 2016, now Pat. No. 10,238,377, which is a continuation of application No. 12/485,878, filed on Jun. 16, 2009, now Pat. No. 9,277,910, and a continuation-in-part of application No. 12/347,831, filed on Dec. 31, 2008, now Pat. No. 9,295,460.

(60) Provisional application No. 61/061,960, filed on Jun. 16, 2008.

(52) U.S. Cl.
CPC ............... *A61B 2017/0412* (2013.01); *A61B 2017/0414* (2013.01); *A61B 2017/0427* (2013.01); *A61B 2017/044* (2013.01); *A61B 2017/0453* (2013.01); *A61B 2017/0456* (2013.01); *A61B 2017/0496* (2013.01); *A61B 2090/037* (2016.02)

(58) Field of Classification Search
CPC .... A61B 2017/0427; A61B 2017/0453; A61B 2017/0456
See application file for complete search history.

(56) References Cited

U.S. PATENT DOCUMENTS

| | | | |
|---|---|---|---|
| 5,702,397 | A | 12/1997 | Goble et al. |
| 5,935,129 | A | 8/1999 | Mcdevitt et al. |
| 5,957,953 | A | 9/1999 | Dipoto et al. |
| 5,968,078 | A | 10/1999 | Grotz |
| 6,143,017 | A | 11/2000 | Thal |
| 6,436,142 | B1 | 8/2002 | Paes et al. |
| 6,527,794 | B1 | 3/2003 | Mcdevitt et al. |
| 6,716,234 | B2 | 4/2004 | Grafton et al. |
| 6,736,234 | B2 | 5/2004 | Zheng et al. |
| 7,144,413 | B2 | 12/2006 | Wilford et al. |
| 7,381,213 | B2 | 6/2008 | Lizardi |
| 7,517,357 | B2 | 4/2009 | Abrams et al. |
| 9,277,910 | B2 * | 3/2016 | Nason ................ A61B 17/0401 |
| 9,295,460 | B2 * | 3/2016 | Hoof ................. A61B 17/0401 |
| 10,238,377 | B2 * | 3/2019 | Nason ................ A61B 17/0401 |
| 11,612,387 | B2 * | 3/2023 | Nason ................ A61B 17/0401 606/232 |
| 2002/0151977 | A1 | 10/2002 | Paes et al. |
| 2005/0033363 | A1 | 2/2005 | Bojarski et al. |
| 2005/0055052 | A1 | 3/2005 | Lombardo et al. |
| 2005/0075668 | A1 | 4/2005 | Lizardi |
| 2006/0259076 | A1 | 11/2006 | Burkhart |
| 2007/0060922 | A1 | 3/2007 | Dreyfuss |
| 2007/0173845 | A1 | 7/2007 | Kim |
| 2007/0203498 | A1 | 8/2007 | Gerber et al. |
| 2008/0004659 | A1 | 1/2008 | Burkhart et al. |
| 2008/0051836 | A1 | 2/2008 | Foerster et al. |
| 2008/0086138 | A1 | 4/2008 | Stone et al. |
| 2008/0109038 | A1 | 5/2008 | Steiner et al. |
| 2008/0208253 | A1 | 8/2008 | Dreyfuss et al. |
| 2008/0249567 | A1 | 10/2008 | Kaplan |
| 2009/0112270 | A1 | 4/2009 | Lunn et al. |
| 2009/0312793 | A1 | 12/2009 | Huxel et al. |
| 2016/0302785 | A1 | 10/2016 | Nason et al. |
| 2019/0167252 | A1 | 6/2019 | Nason et al. |

FOREIGN PATENT DOCUMENTS

| | | |
|---|---|---|
| EP | 2224858 A1 | 9/2010 |
| FR | 2846867 A1 | 5/2004 |
| WO | WO-2009055800 A1 | 4/2009 |
| WO | WO-2009146155 A1 | 12/2009 |
| WO | WO-2010009184 A1 | 1/2010 |

OTHER PUBLICATIONS

U.S. Appl. No. 12/485,878 U.S. Pat. No. 9,277,910, filed Jun. 16, 2009, Anchors and Method for Securing Suture to Bone.
U.S. Appl. No. 15/046,414 U.S. Pat. No. 10,238,377, filed Feb. 17, 2016, Anchors and Methods for Securing Suture to Bone.
U.S. Appl. No. 16/269,215, filed Feb. 6, 2019, Anchors and Methods for Securing Suture to Bone.
"U.S. Appl. No. 12/485,878, 312 Amendment filed Dec. 11, 2015", 3 pgs.
"U.S. Appl. No. 12/485,878, Advisory Action mailed Oct. 2, 2012", 3 pgs.
"U.S. Appl. No. 12/485,878, Final Office Action mailed Jul. 17, 2012", 9 pgs.
"U.S. Appl. No. 12/485,878, Final Office Action mailed Nov. 13, 2014", 7 pgs.
"U.S. Appl. No. 12/485,878, Non Final Office Action mailed Jan. 31, 2014", 10 pgs.
"U.S. Appl. No. 12/485,878, Non Final Office Action mailed Jun. 17, 2015", 9 pgs.
"U.S. Appl. No. 12/485,878, Non Final Office Action mailed Sep. 2, 2011", 7 pgs.
"U.S. Appl. No. 12/485,878, Notice of Allowance mailed Oct. 23, 2015", 7 pgs.
"U.S. Appl. No. 12/485,878, PTO Response to Rule 312 Communication mailed Dec. 14, 2015", 2 pgs.
"U.S. Appl. No. 12/485,878, Response filed Mar. 2, 2012 to Non Final Office Action mailed Sep. 2, 2011", 8 pgs.
"U.S. Appl. No. 12/485,878, Response filed Apr. 13, 2015 to Final Office Action mailed Nov. 13, 2014", 12 pgs.
"U.S. Appl. No. 12/485,878, Response filed Jul. 30, 2014 to Non Final Office Action mailed Jan. 31, 2014", 10 pgs.
"U.S. Appl. No. 12/485,878, Response filed Sep. 16, 2015 to Non Final Office Action mailed Jun. 17, 2015", 6 pgs.
"U.S. Appl. No. 12/485,878, Response filed Sep. 17, 2012 to Final Office Action mailed Jul. 17, 2012", 10 pgs.
"U.S. Appl. No. 15/046,414, Final Office Action mailed Aug. 29, 2018", 7 pgs.
"U.S. Appl. No. 15/046,414, Non Final Office Action mailed Mar. 2, 2018", 9 pgs.
"U.S. Appl. No. 15/046,414, Notice of Allowability mailed Feb. 15, 2019", 2 pgs.
"U.S. Appl. No. 15/046,414, Notice of Allowance mailed Nov. 6, 2018", 5 pgs.
"U.S. Appl. No. 15/046,414, Response filed Jun. 4, 2018 to Non Final Office Action mailed Mar. 2, 2018", 14 pgs.
"U.S. Appl. No. 15/046,414, Response filed Oct. 29, 2018 to Final Office Action mailed Aug. 29, 2018", 8 pgs.
"U.S. Appl. No. 16/269,215, Advisory Action mailed Nov. 9, 2021", 3 pgs.
"U.S. Appl. No. 16/269,215, Final Office Action mailed Sep. 3, 2021", 14 pgs.
"U.S. Appl. No. 16/269,215, Final Office Action mailed Sep. 12, 2022", 15 pgs.
"U.S. Appl. No. 16/269,215, Non Final Office Action mailed Feb. 26, 2021", 13 pgs.
"U.S. Appl. No. 16/269,215, Non Final Office Action mailed May 12, 2022", 15 pgs.
"U.S. Appl. No. 16/269,215, Notice of Allowance mailed Nov. 23, 2022", 9 pgs.
"U.S. Appl. No. 16/269,215, Preliminary Amendment filed Feb. 7, 2019", 5 pgs.
"U.S. Appl. No. 16/269,215, Response filed May 26, 2021 to Non Final Office Action mailed Feb. 26, 2021", 12 pgs.
"U.S. Appl. No. 16/269,215, Response filed Aug. 12, 2022 to Non Final Office Action mailed May 12, 2022", 13 pgs.
"U.S. Appl. No. 16/269,215, Response filed Oct. 31, 2022 to Final Office Action mailed Sep. 12, 2022", 13 pgs.
"U.S. Appl. No. 16/269,215, Response filed Nov. 3, 2021 to Final Office Action mailed Sep. 3, 2021", 13 pgs.
"Australian Application Serial No. 2009268951, First Examiners Report mailed Feb. 4, 2014", 4 pgs.
"Australian Application Serial No. 2009268951, Response filed Jul. 31, 2014 to First Examiners Report mailed Feb. 4, 2014", 19 pgs.

(56) References Cited

OTHER PUBLICATIONS

"European Application Serial No. 09794941.6, Communication Pursuant to Article 94(3) EPC mailed Jan. 22, 2015", 4 pgs.
"European Application Serial No. 09794941.6, Communication Pursuant to Article 94(3) EPC mailed Aug. 24, 2016", 5 pgs.
"European Application Serial No. 09794941.6, Communication Pursuant to Article 94(3) EPC mailed Sep. 30, 2015", 6 pgs.
"European Application Serial No. 09794941.6, Communication Pursuant to Article 94(3) EPC mailed Oct. 12, 2017", 5 pgs.
"European Application Serial No. 09794941.6, Extended European Search Report mailed Jan. 2, 2014", 6 pgs.
"European Application Serial No. 09794941.6, Response filed Mar. 30, 2016 to Communication Pursuant to Article 94(3) EPC mailed Sep. 30, 2015", 6 pgs.
"European Application Serial No. 09794941.6, Response filed May 22, 2015 to Communication Pursuant to Article 94(3) EPC mailed Jan. 22, 2015", 6 pgs.
"European Application Serial No. 09794941.6, Response filed Jul. 15, 2014 to Extended European Search Report mailed Jan. 2, 2014", 8 pgs.
"European Application Serial No. 09794941.6, Response filed Nov. 21, 2017 to Communication Pursuant to Article 94(3) EPC mailed Oct. 12, 2017", 5 pgs.
"European Application Serial No. 09794941.6, Response filed Dec. 28, 2016 to Communication Pursuant to Article 94(3) EPC mailed Aug. 24, 2016", 4 pgs.
"European Application Serial No. 18183954.9, Response filed Feb. 28, 2022 to Communication Pursuant to Article 94(3) EPC mailed Aug. 19, 2021", 4 pgs.
"European Application Serial No. 18183954.9, Communication Pursuant to Article 94(3) EPC mailed Aug. 19, 2021", 6 pgs.
"European Application Serial No. 18183954.9, Extended European Search Report mailed Jan. 3, 2019", 8 pgs.
"European Application Serial No. 18183954.9, Response filed Jul. 23, 2019 to Extended European Search Report mailed Jan. 3, 2019", 7 pgs.
"Indian Application Serial No. 195/CHENP/2011, Office Action Mailed Mar. 9, 2018", (W/ English Translation), 9 pgs.
"Indian Application Serial No. 195/CHENP/2011, Response filed Sep. 3, 2018 to Office Action Mailed Mar. 9, 2018", (W/ English Translation), 7 pgs.
"International Application Serial No. PCT/US2009/047570, International Preliminary Report on Patentability mailed Dec. 29, 2010", 7 pgs.
"International Application Serial No. PCT/US2009/047570, International Search Report mailed Oct. 2, 2009", 3 pgs.
"International Application Serial No. PCT/US2009/047570, Written Opinion mailed Oct. 2, 2009", 5 pgs.
"European Application Serial No. 18183954.9, Invitation pursuant to Article 94(3) and Rule 71(1) EPC mailed Jun. 4, 2024", 6 pgs.

* cited by examiner

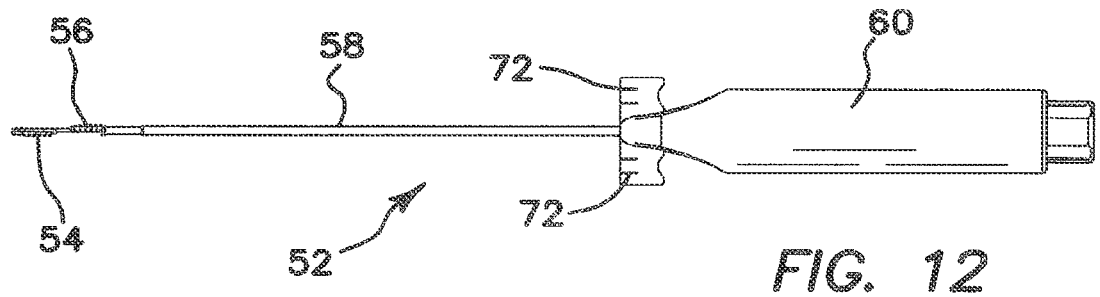
FIG. 12
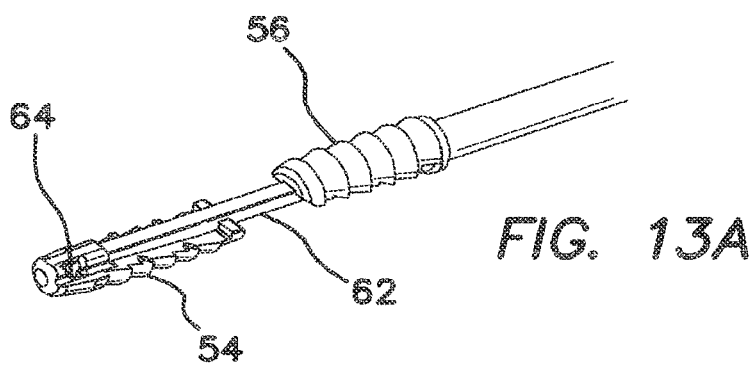
FIG. 13A
FIG. 13B
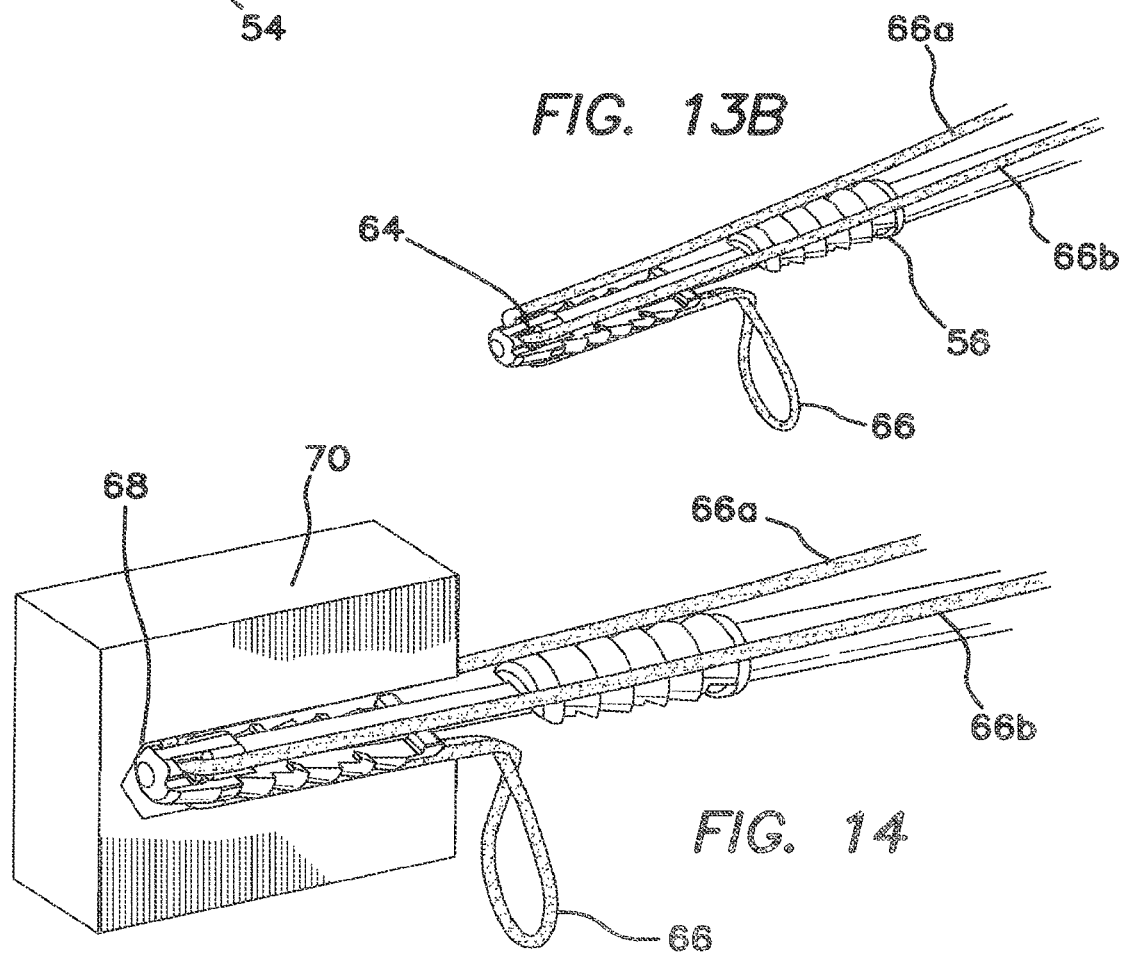
FIG. 14

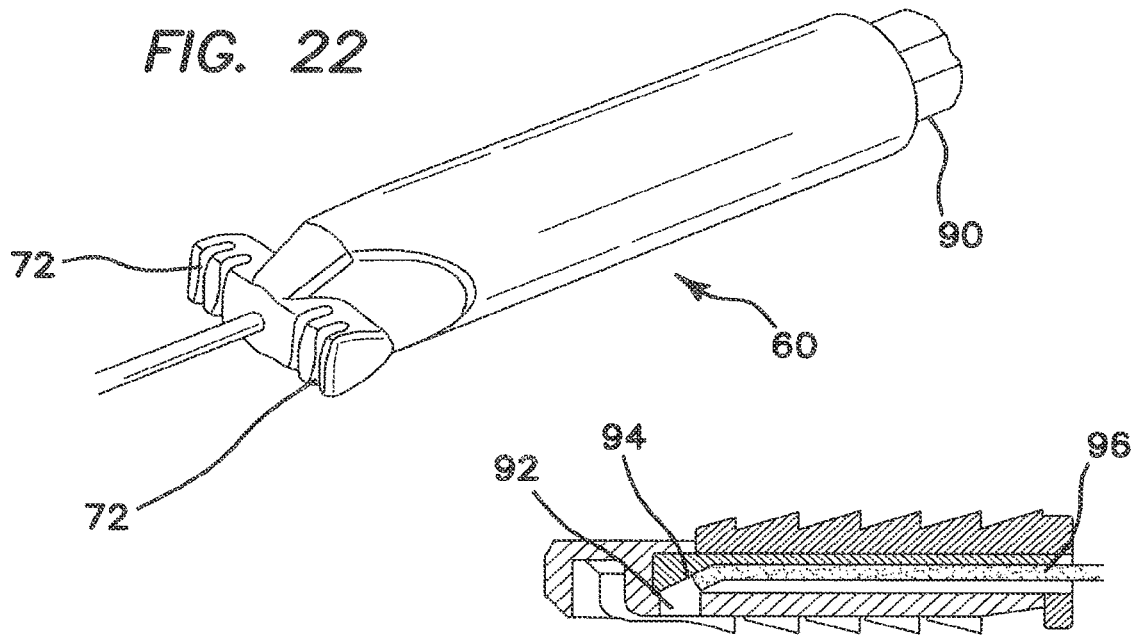
FIG. 22
FIG. 23A
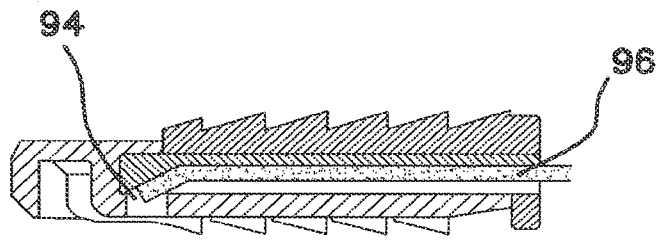
FIG. 23B
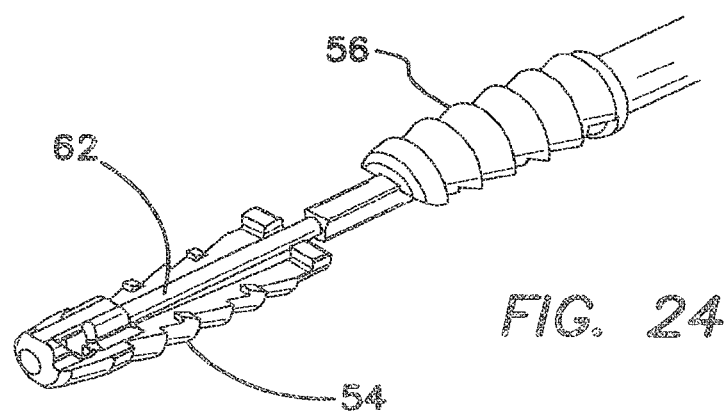
FIG. 24

ANCHORS AND METHODS FOR SECURING SUTURE TO BONE

This application is a continuation under 35 U.S.C. 120 of commonly assigned U.S. patent application Ser. No. 12/485,878, entitled Anchors and Methods for Securing Suture to Bone, filed on Jun. 16, 2009 and now allowed, which in turn is a continuation-in-part under 35 U.S.C. 120 of commonly assigned U.S. patent application Ser. No. 12/347,831, entitled Anchors and Method for Securing Suture to Bone, filed on Dec. 31, 2008 and now allowed. U.S. patent application Ser. No. 12/485,878 also claims the benefit under 35 U.S.C. 119(e) of the filing date of Provisional U.S. Application Ser. No. 61/061,960, entitled Devices, Systems, and Methods for Material Fixation, filed on Jun. 16, 2008. Each of these prior patent applications are expressly incorporated herein by reference, in their entirety.

BACKGROUND OF THE INVENTION

The present invention is generally related to the field of suture anchors. There are many procedures, such as SLAP (Superior Labrum from Anterior to Posterior) and Bankart lesion repairs, or reconstruction of labral tissue to the glenoid rim, in which a surgeon needs to secure tissue in close contact with bone. Often the bone surface is roughened, and when tissue is pulled into intimate contact, the body's healing response will fuse the tissue and bone together.

This procedure is often accomplished by implanting an anchor, pre-loaded with a strand of suture, into a hole drilled in the bone at the desired anchor location. One of the suture ends is then passed through the soft tissue at the desired location, and the suture is secured to the anchor by tying a knot.

There are many suture anchor designs on the market today intended to secure suture, which is passed through soft tissue, to bone. Most of the anchor designs rely on interference between external features on the anchor (barbs, ribs, ridges, etc.) and the hole to provide fixation strength. A high amount of interference results in a large force required to insert the anchor into the bone. These large insertion forces (often imparted by a hammer or mallet) can result in broken anchors, broken insertion tools, or worse, damage to the bone itself. An important step in the procedure is adding tension to the suture to pull the captured tissue into intimate contact with the bone. Many anchors can change the tension in the suture during deployment, which requires the surgeon to estimate how much tension will be added during the final installation step. This can result in under- or over-tensioning of the tissue against the bone. The final step of securing the suture and tissue—tying a knot—has been shown to be a common source of anchor failure. It is also a step that requires a great deal of practice and skill by the surgeon and time during the procedure itself.

Since the knot is often problematic for the reasons stated above, several knotless designs have recently been developed. Some of these are described below:

The Bioknotless™ anchor by DePuy Mitek is a simple anchor which is loaded with a loop of suture secured to the anchor with a knot. The loop is passed through the tissue, then the loop must be hooked in a groove at the tip of the anchor. This step can be tedious and difficult, depending on the angle of approach to the hole. Finally, the anchor is tapped into the hole in the bone. The final tension on the suture loop and attached tissue is controlled by the anchor insertion depth. This requires the surgeon to drill a hole deep enough to achieve sufficient tension. If the bite of tissue through which suture is passed is smaller than expected or achievable, the anchor may reach the bottom of the hole before enough tension is placed on the tissue. This results in the tissue not being pulled firmly against the bone surface and may result in inferior long-term repair strength. Depending on the angle of approach and the location on the bone (such as inferior on the glenoid), it may be impossible to drill a deep enough hole to achieve the desired tension.

Arthrocare has developed the LabraLock P™ anchor. This two-part anchor, made from PEEK (Polyetheretherketone), secures two strands of suture (the strands which form the loop that is passed through the tissue) between the anchor and the bone, and the other two strands (the free ends of suture) between the anchor's inner shaft and the outer, tube portion. The outer tube portion has barbs which secure the anchor in the bone via an interference fit.

The PushLock™ anchor, by Arthrex, is also a two-part anchor. The tip of the anchor has an eyelet through which the suture legs are loaded. This tip is placed at the bottom of a hole drilled into the bone. At this point, the surgeon may adjust the tension on the suture, thereby pulling the tissue closer to the surface of the bone. When the tension is deemed correct, the rear portion of the anchor is driven into the hole. This rear portion is a length of tube which has circumferential barbs on its outer diameter which provide interference to anchor the device in the hole. Since the barbed portion of the anchor is a full cylinder, it can require a great deal of force to insert into a smaller diameter hole, especially in hard bone.

The ConMed Ultrafix Knotless Minimite™ anchor is a knotless anchor made of metal, which many surgeons do not want to deploy within a joint. If the anchor were to pull out of the bone, the metal could cause a great deal of damage rubbing against the articular surfaces—e.g. the humeral head and glenoid.

Smith & Nephew has marketed the KINSA™ suture anchor. It is a knotless design made of PEEK which is tapped into a pre-drilled hole in the bone. The anchor is preloaded with suture tied in a one-way sliding knot within the anchor body, which allows the surgeon to adjust the tension after the anchor has been deployed.

SUMMARY OF THE INVENTION

The anchor described in the current invention incorporates several features which make it simple and consistent for the surgeon to implant. In particular, the current designs allow the surgeon to adjust the tension on the suture strands, thus approximating the captured tissue to the anchor location prior to securing the anchor and suture. Additionally, when the anchor is locked into the bone, the tension on the suture and captured tissue does not change.

Another advantage of the current designs is that they eliminate the need for the surgeon to tie a knot. The performance of the knot is dependent upon many factors—the skill of the surgeon, the type of suture material, the ease of access to the knot location, etc. Tying a secure knot often requires several knots, such as a Duncan Loop backed up by alternating half-hitches. Each of these must be pulled tight with a knot pusher to secure them properly. Securing the suture between the anchor and bone is much less time consuming and less prone to surgeon error or variability.

More particularly, an anchoring system for securing suture to bone is provided which comprises an implant including a distal tip having a suture securing portion, preferably a suture eyelet, and having external surface features for securing the implant within surrounding bone, and also including a proximal member which is movable distally to engage the distal tip and to fix the suture in place within the implant and relative to the bone. The anchoring system further comprises an inserter which is removably connectable to a proximal end of the implant. The proximal member preferably comprises a screw member having a central bore. The inserter comprises an inserter tip which is configured to slide through the central bore of the screw member.

The inserter tip further comprises a threaded distal tip which is adapted to engage a corresponding threaded hole in a proximal end of the distal tip. The threads in the threaded hole are left-handed. A handle portion is connected to a proximal end of the inserter. A suture channel is disposed on an external surface of the implant for permitting the suture to slide freely along the external surface for tissue tensioning. These external surface features preferably comprise ribs, which are preferably triangular-shaped. The inserter further comprises an insertion sleeve for pushing the proximal member distally over the inserter tip. The inserter further comprises a handle.

The handle, in turn, preferably comprises a plurality of suture cleats, as well as a knob which is actuatable to engage the proximal screw to the distal tip.

In another aspect of the invention, there is disclosed a method for securing suture to bone, which comprises steps of drilling a hole in a desired portion of bone at a desired procedural site, passing a strand of suture through a portion of soft tissue to be approximated to the portion of bone, and extending the free suture ends proximally from the soft tissue. Additional inventive steps comprise loading the suture into a distal tip of an anchor implant, using an inserter, on a distal end of which is attached the distal tip, to manipulate the distal tip into the bone hole, and tensioning the suture to a desired level by pulling on the free suture ends, after the distal tip is positioned in the bone hole. The free suture ends are then wrapped about a suture cleat on an inserter handle once the desired tension level is achieved. A proximal anchor component is engaged with the distal tip to lock the anchor in place within the bone hole, and to lock the suture in place within the anchor. When the procedure is complete, the inserter is removed from the procedural site.

An additional procedural step comprises a step of trimming the free suture ends. Preferably, the loading step comprises placing the suture through a suture eyelet in the distal tip. The proximal anchor component comprises a screw with external threads, and the engaging step comprises advancing the proximal anchor component to the entrance of the bone hole, then rotating the end of the inserter to screw the proximal anchor component into the bone hole. The proximal anchor component is advanced by pushing it with an insertion sleeve.

In yet another aspect of the invention, there is disclosed a suture anchoring system which comprises a suture anchor comprising a distal tip and a proximal screw, as well as an inserter which is removably connectable to a proximal end of the suture anchor. The distal tip and the proximal screw are separate structural components which are engageable together to form the suture anchor. The proximal screw comprises a central bore. The inserter comprises an inserter tip which is configured to slide through the central bore of the proximal screw.

The inserter tip further comprises a threaded distal tip which is adapted to engage a corresponding threaded hole in a proximal end of the distal tip. The threads in the threaded hole are left-handed.

A handle portion is connected to a proximal end of the inserter. The inserter further comprises an insertion sleeve for pushing the proximal screw distally over the inserter tip. The handle comprises a plurality of suture cleats, as well as a knob which is actuatable to engage the proximal screw to the distal tip.

The invention, together with additional features and advantages thereof, may best be understood by reference to the following description taken in conjunction with the accompanying illustrative drawing.

BRIEF DESCRIPTION OF THE DRAWINGS

FIG. 12 is a plan view of another modified embodiment of an inserter and suture anchor constructed in accordance with the principles of the present invention;

FIG. 13A is an isometric view of the distal tip of the suture anchor of FIG. 12;

FIG. 13B is a view similar to FIG. 13A illustrating the anchor loaded with suture;

FIG. 14 is an isometric view showing the distal tip of the suture anchor of FIGS. 12-13B as it is inserted into a drilled hole (socket) in bone;

FIG. 22 is an isometric view of the inserter handle of the embodiment of FIGS. 12-20B;

FIG. 23A is a cross-sectional side view of a modified embodiment of the inserter tip shown in FIGS. 12-21, with the wire lock in an unlocked position;

FIG. 23B is a cross-sectional side view of the embodiment of FIG. 23A, wherein the wire lock is in a locked position;

FIG. 24 is an isometric view of still another modified embodiment of the inserter tip of FIGS. 12-21;

DESCRIPTION OF THE PREFERRED EMBODIMENT

Figure 1:
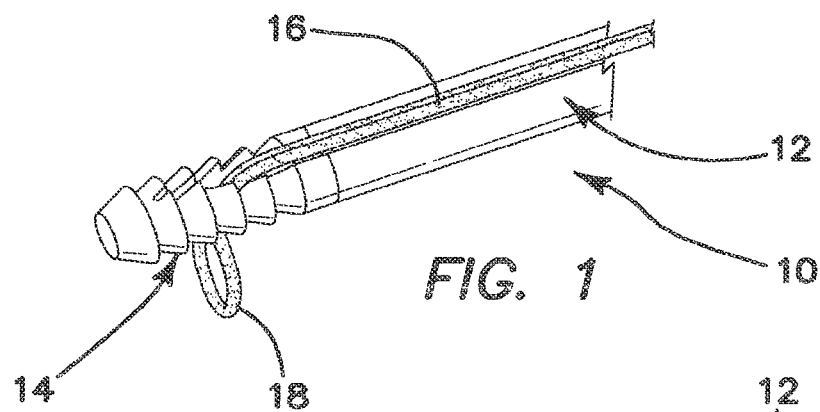
FIG. 1 is a distal end view of one embodiment of a "suture first" suture-to-bone implantable anchor constructed in accordance with the principles of the present invention.
Figure 2:
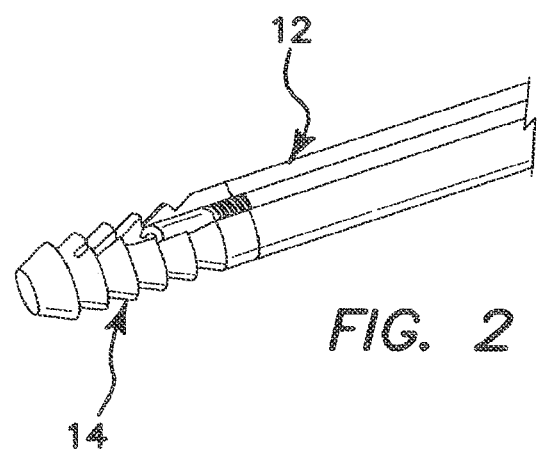
FIG. 2 is a view similar to FIG. 1, after suture has been snared by the inventive device and pulled proximally through an eyelet in the implant.
Figure 3:
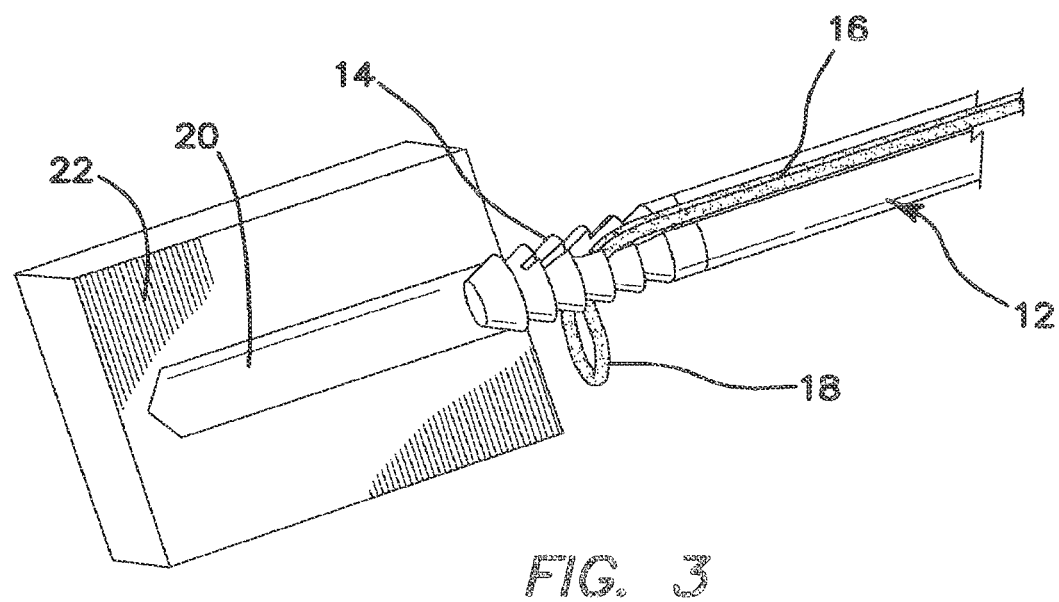
FIG. 3 is a view similar to FIGS. 1 and 2, showing the inventive device being inserted into a drilled bone hole.
Figure 4:
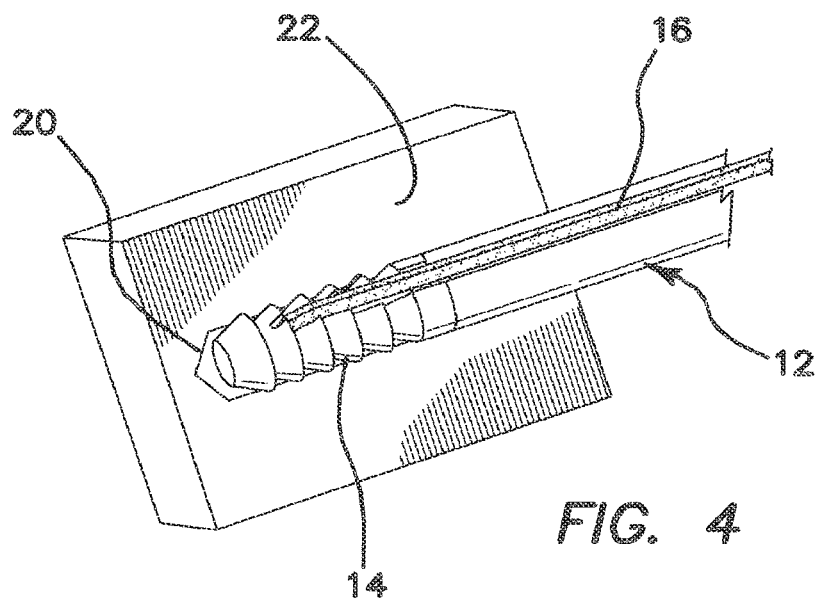
FIG. 4 is a view similar to FIG. 3, illustrating the inventive device after it has been advanced to a distal end of the bone hole.
Figure 5:
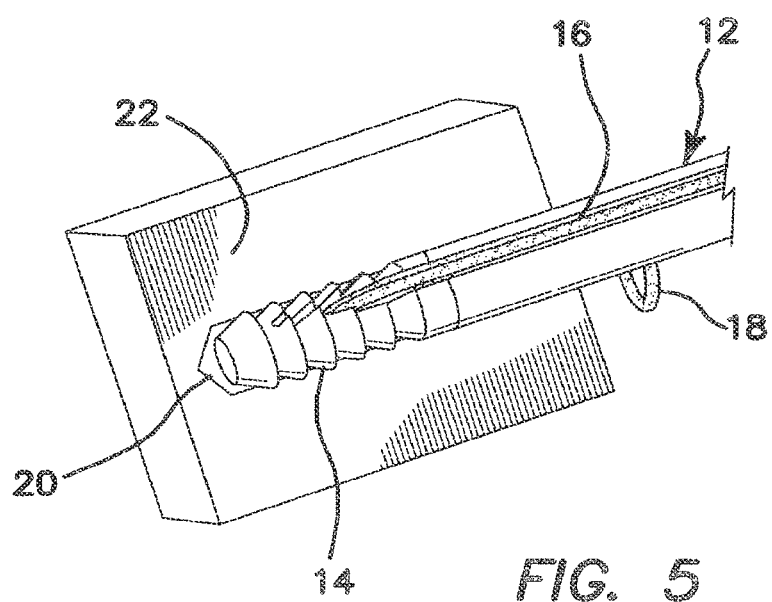
FIG. 5 is a view similar to FIGS. 3 and 4, illustrating the device after the suture has been tensioned by the practitioner to approximate the captured tissue to the anchor location.

Referring now more particularly to the drawings, there is shown in FIGS. 1-5 the distal end of a "suture first" suture to bone implantable anchoring device 10. The device 10 comprises an inserter 12, and an implant 14 loaded on the tip of the inserter 12. Suture 16 is disposed along the inserter 12, as shown in FIG. 1, for example, and through the implant 14, with a loop 18 of suture extending therefrom. This loop 18 is the loop of suture which would extend through the tissue to be approximated to the bone, which is not shown, for clarity. Also not shown in this figure is a suture snare that is used to pull the suture loop 18 into a suture eyelet in the middle of the implant 14, which is illustrated and described below. The snare may comprise a loop of nitinol wire or suture, insert molded into a plastic pull-tab (not shown) which may be mounted on the shaft of the inserter 12. Once the suture strands are placed into the suture snare, the pull-tab is removed from the inserter shaft and pulled proximally to ensnare the suture strands and pass them through the eyelet in the implant. FIG. 2 illustrates the inserter 12 and implant 14 after the suture has been passed through the implant eyelet. In accordance with a method of the invention, the inserter 12 of FIG. 1 is slid along the suture 16 distally and through an arthroscopic portal into the patient's body, in the vicinity of the desired procedural site. The distal tip of the implant is then inserted into a hole or tunnel 20 (FIG. 3) which has been pre-drilled in a selected bone portion 22, and advanced until it is flush with the bottom of the hole 20 (FIG. 4). At this point, the surgeon can pull on the free ends of the suture 16, which have remained outside of the arthroscopic portal (not shown), to tension the suture 16 and thereby approximate captured tissue (not shown) to the anchor location. The device after the suture has been tensioned by the surgeon to approximate the captured tissue to the anchor location is illustrated in FIG. 5.

Figure 6A:
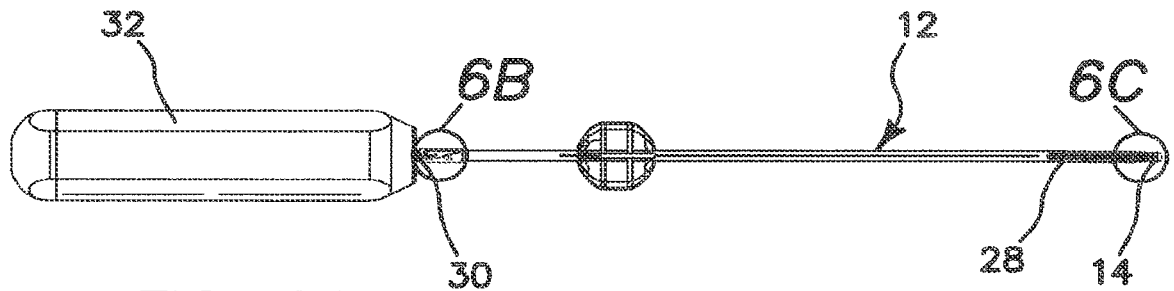
FIG. 6A is a plan view illustrating an inserter for use with the implant of FIGS. 1-5.
Figure 6B:
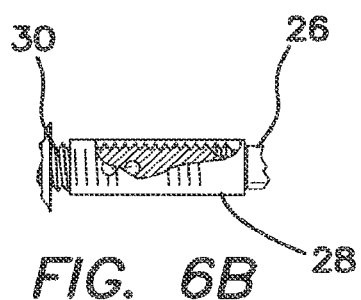
FIG. 6B is a detail view of the portion denoted by circle B in FIG. 6A.
Figure 6C:
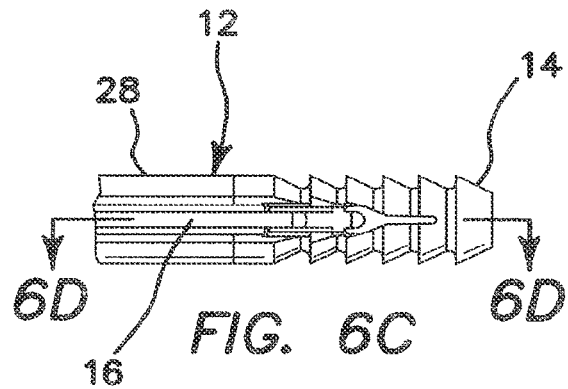
FIG. 6C is a detail view of the portion denoted by circle A in FIG. 6A.
Figure 6D:
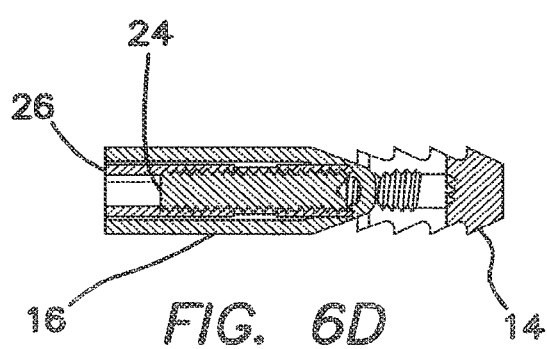
FIG. 6D is a cross-sectional view taken along lines 6D-6D in FIG. 6C.
Figure 7A:
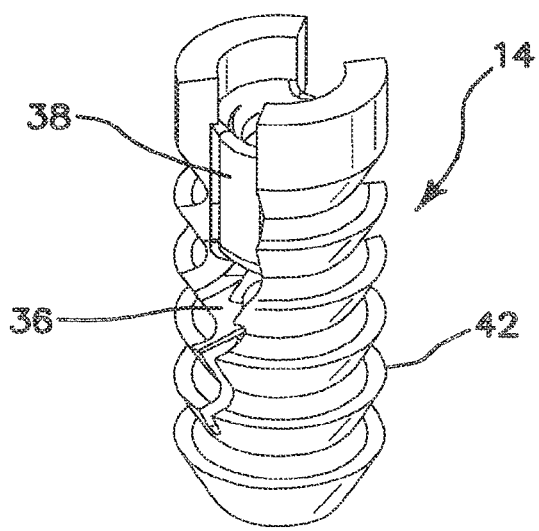
FIG. 7A is an isometric view of the insertion shaft forming a portion of the inserter illustrated in FIG. 6A.
Figure 7B:
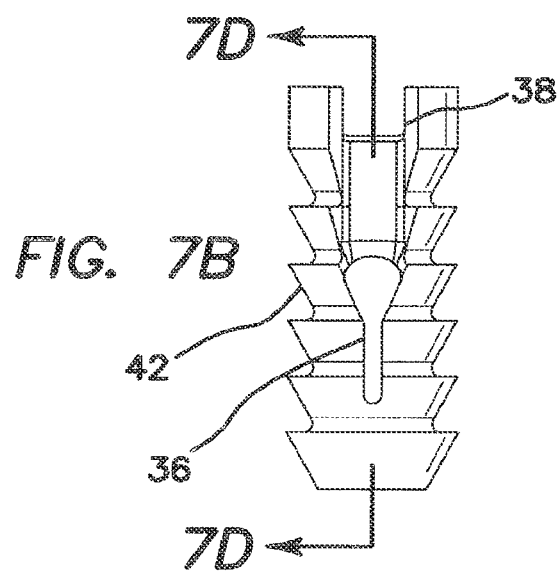
FIG. 7B is a plan view of the insertion shaft of FIG. 7A.
Figure 7C:
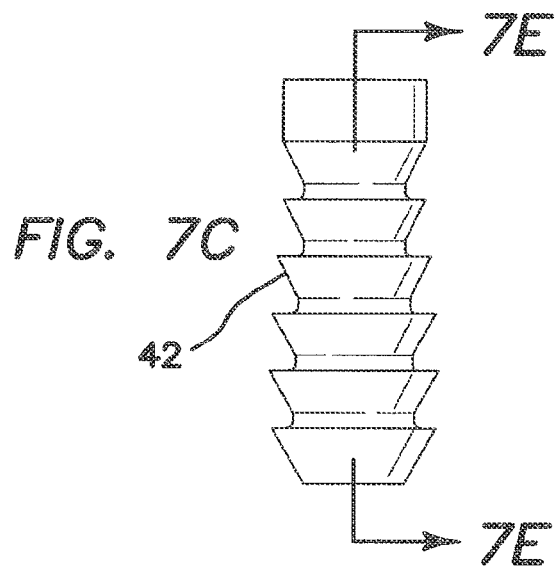
FIG. 7C is a plan view similar to FIG. 7B, rotated approximately 90 degrees.
Figure 7D:
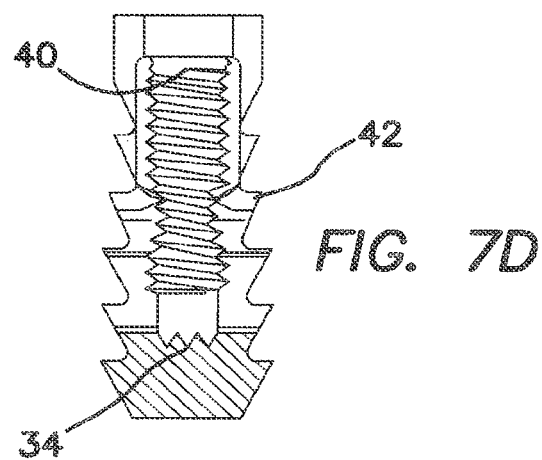
FIG. 7D is a cross-sectional view taken along lines 7D-7D of FIG. 7B.
Figure 7E:
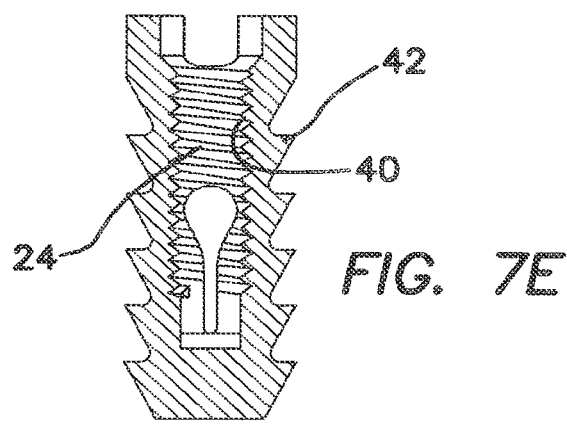
FIG. 7E is a cross-sectional view taken along lines 7E-7E of FIG. 7C.
Figure 7F:
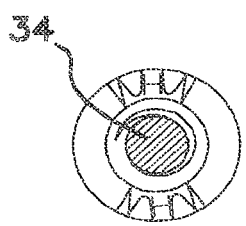
FIG. 7F is a top end view of the inserter shown in FIG. 7B.
Figure 7G:
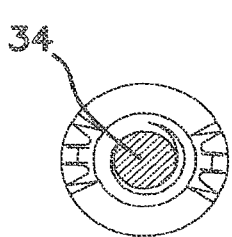
FIG. 7G is a top end view of the inserter shown in FIG. 7C.
Figure 7H:
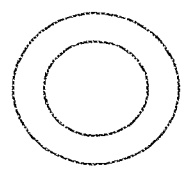
FIG. 7H is a bottom end view of the inserter shown in FIG. 7B.

FIGS. 6A-6D illustrate an embodiment of a simple insertion device which may be used in conjunction with the device 10. It is noted that the implant 14 may be comprised of a biocompatible material, such as PEEK. FIG. 6C illustrates the implant in its suture-loaded configuration, ready for insertion into the bone drill hole and ready for deployment. As shown in FIG. 6D, the implant further comprises a screw 24, which is retained only partially within the implant 14 prior to deployment. An engagement tube 26 is also disposed within the implant 14. Its purpose is to tighten the screw 24, and to couple the screw and implant 14 to the insertion device 12. The tip of the engagement tube 26 is threaded to engage with the top of the screw 24. The inserter or insertion device 12 comprises an insertion shaft 28. The insertion shaft functions to transfer a load from the insertion device 12 to the top of the implant 14, thereby allowing the implant 14 to be hammered or pushed into the drill hole 20. The insertion shaft 28 engages with the engagement tube 26 by means of a threaded engagement 30 between the insertion shaft 28 and the engagement tube 26 at a proximal end of the inserter 12 (FIG. 6B and Detail B of FIG. 6A). The thread between the insertion shaft and the engagement tube is in a 1:1 ratio with the PEEK screw 24 in the implant, so that the travel distance of the PEEK screw 24 and the engagement tube 26 remains the same. Moreover, the travel distance is adjustably limited by the threaded portion 30 shown in FIG. 6B.

Proximal to the threaded portion 30, is a handle portion 32, for permitting manipulation and rotation of the device 10, as desired.

There are two potential modes of removal of the insertion device 12 from the implant 14, after deployment. In one such mode, after deployment of the implant by tightening the screw 24, the screw can be purposely over-tightened, thus breaking the screw 24 off from the implant 14. Testing has shown that the screw 24 does not need to be made specifically "frangible" for this method to work repeatedly, as torsional stress are always the highest in the PEEK screw 24 at the tip of the engagement tube 26.

Another mode for removal assumes that after deployment or tightening of the screw 24, the frictional forces of the suture 16 against the screw 24 are high enough to prevent the screw 24 from loosening while the engagement tube 26 is rotated in the anti-deployment direction to loosen its threads from the PEEK screw 24. Of course, other suitable removal modes may be utilized as well.

FIGS. 7A-7H illustrate in greater detail constructional features of the implant 14. In particular, the implant 14 comprises internal surface texturing 34 at a pinch point within the implant, for improving suture retention after fixation. The internal surface texturing may comprise spikes, knurling, or other known biting surfaces of that nature.

A suture eyelet or cleat 36 is provided within the implant. The suture loads through the eyelet with the use of a suture snare, as was described above. During deployment, the suture get pushed within the cleat, which bites into the suture for retention. A suture channel 38 allows the suture to slide freely along the external walls of the implant 14 for tissue tensioning. In practice, the implant 14 is inserted into the bone tunnel 20, and desired tension is achieved by manually pulling on the suture strands. Once the desired tension is achieved, the screw 24 locks the suture in place.

An internal thread 40 is provided within the PEEK implant 14. The mating screw 24 creates a pinch force, locking the suture into place after tensioning. The thread also serves as a retention mechanism for attaching the implant and screw to the insertion device 12. A plurality of frustoconical surfaces or barbs 42 serve to retain the implant and resist pullout from adjacent bone.

Figure 8A:
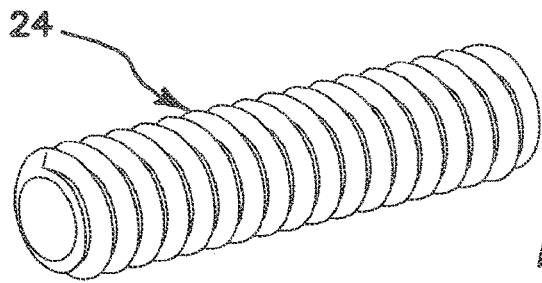
FIG. 8A is an isometric view of a mating screw used in connection with the embodiment of FIG. 1.
Figure 8B:
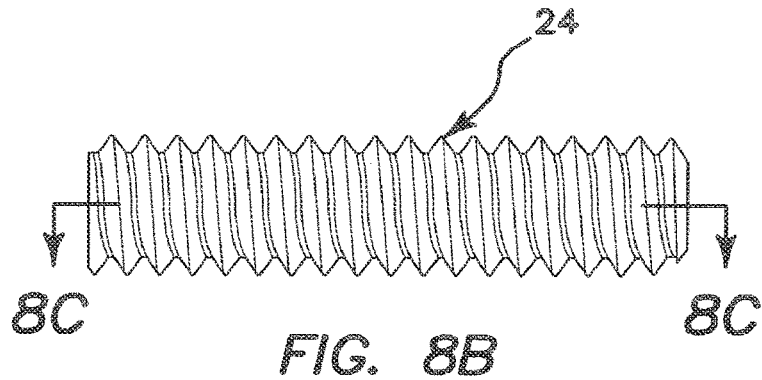
FIG. 8B is a plan view of the screw of FIG. 8A.
Figure 8C:
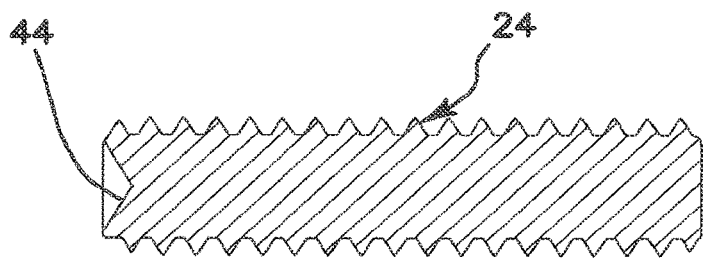
FIG. 8C is a cross-sectional view taken along lines 8C-8C of FIG. 8B.

FIGS. 8A-8C illustrate in greater detail the mating screw 24. As noted above, tightening of the screw within the implant 14 locks the suture into place by pinching it against the bottom of the anchor and also by forcing it into the suture cleats connected to the suture eyelet. The bottom 44 of the screw 24 may be knurled, cupped, or pointed to increase the pinching force that locks the suture into place.

Figure 9:
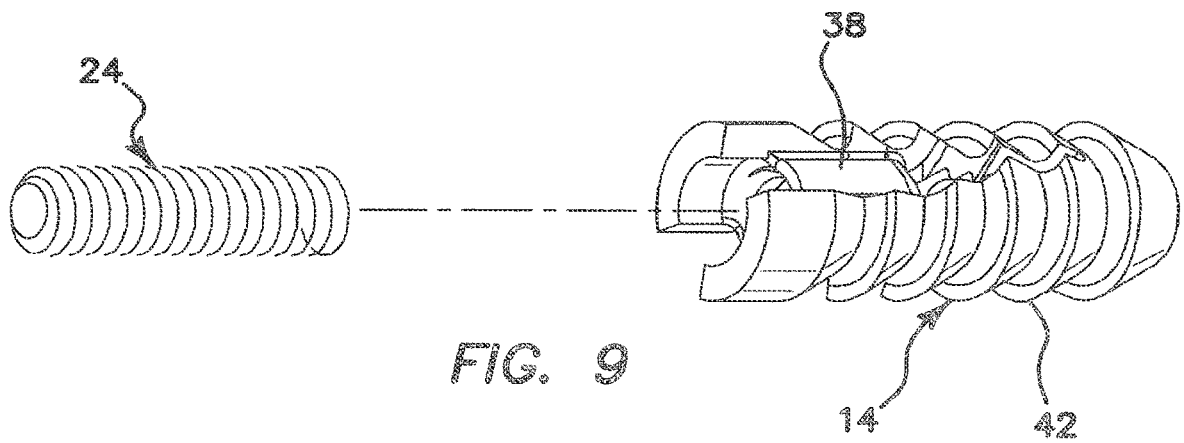
FIG. 9 is an exploded view of the suture anchor and screw of the embodiment of FIGS. 1-8C.
Figure 10A:
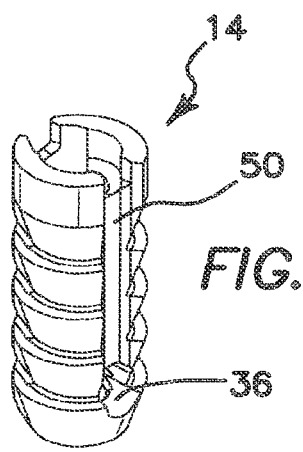
FIG. 10A is an isometric view of a modified embodiment of the inventive implant.
Figure 10B:
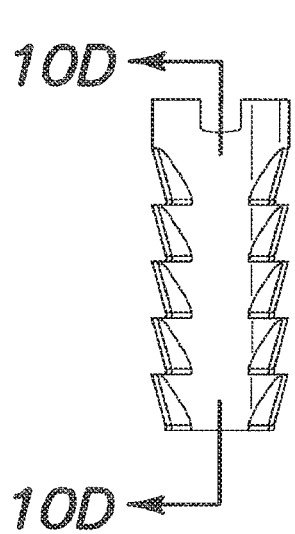
FIG. 10B is a plan view of the implant of FIG. 10A.
Figure 10C:
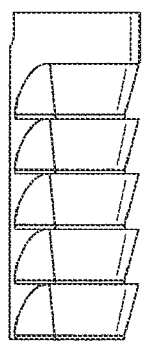
FIG. 10C is a plan view similar to FIG. 10B, rotated approximately 90 degrees relative to FIG. 10B.
Figure 10D:
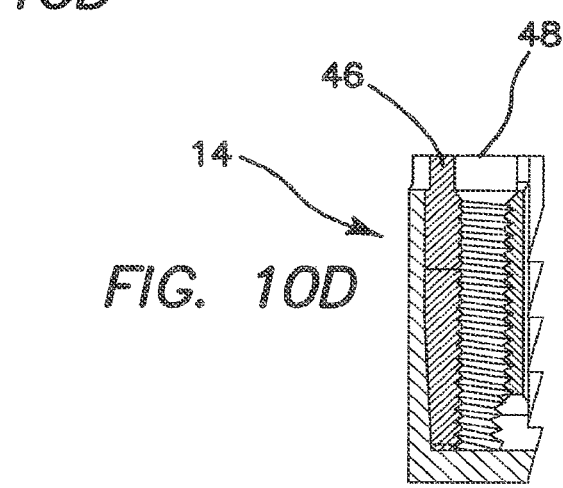
FIG. 10D is a cross-sectional view taken along the lines 10D-10D of FIG. 10B.
Figure 10E:
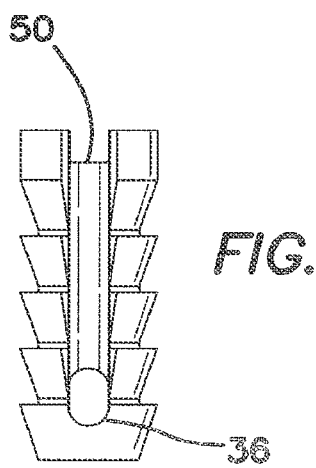
FIG. 10E is a plan view similar to FIG. 10B, rotated approximately 180 degrees relative to FIG. 10B.
Figure 10F:
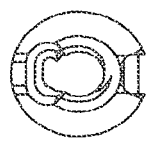
FIG. 10F is a top view of the implant illustrated in FIG. 10C.
Figure 11A:
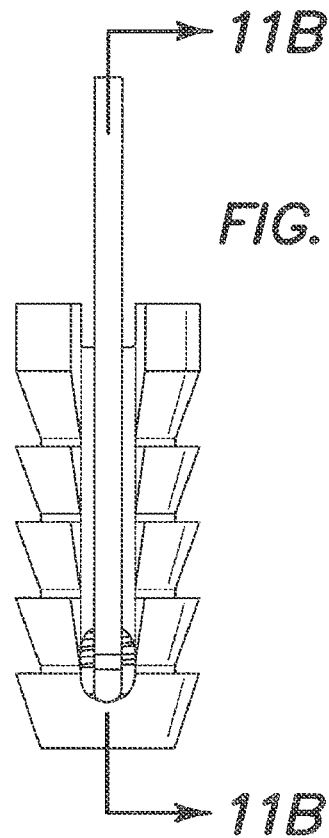
FIG. 11A is a plan view similar to FIG. 10E, after suture has been deployed therein.
Figure 11B:
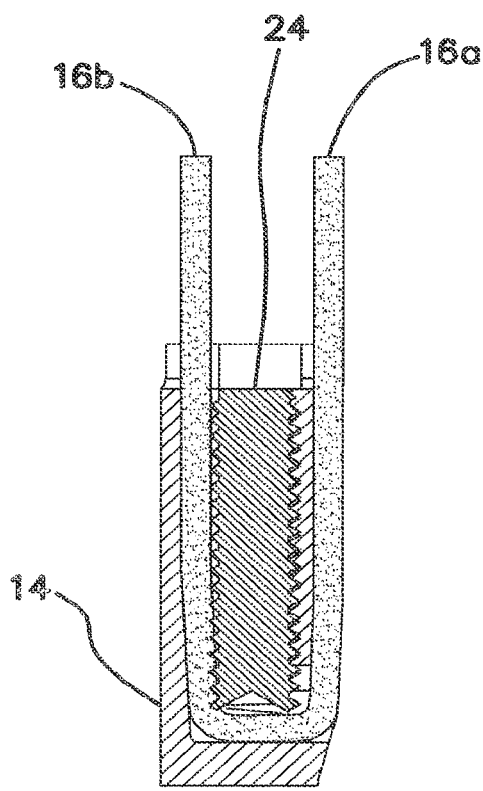
FIG. 11B is a cross-sectional view taken along lines 11B-11B of FIG. 11A.
Figure 11C:
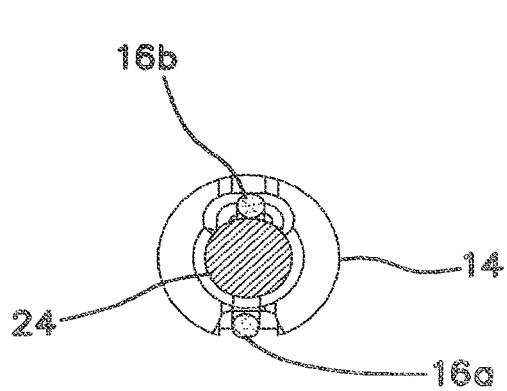
FIG. 11C is a top view of the implant illustrated in FIG. 11B.

FIG. 9 is an exploded view of the implant 14 and screw 24, shown, for clarity, without suture and not attached to the insertion device 12.

A modified embodiment of the implant 14 is illustrated in FIGS. 10A-11C. In this embodiment, rather than having the suture being pinched solely at the bottom of the implant 14, this embodiment features one leg 16a of the suture running on the external side of the implant, while the other leg 16b of the suture remains inside of the implant to be compressed against the screw 24 and along the tapered edge of a suture cavity 46. The implant is threaded, as in the prior embodiment, but because of the tapered internal cavity 46 inside one half of the implant, the thread is not fully circumferential. Instead, it extends downwardly along a "C" shaped screw portion 48. The PEEK screw 24 still couples the implant to the inserter, in the same manner as the device of FIGS. 1-9. The internal cavity is tapered to allow the suture to slide freely for tensioning up until the point that the screw is tightened fully. A single suture channel 50 permits the suture to slide freely through the suture eyelet 36, after placing the implant 14 and suture into the drill hole 20 in the bone 22. Upon tightening of the screw 24, the suture 16 is effectively squeezed along the internal tapered cavity 46 and screw 24, thus locking the suture in place.

Returning again to a discussion of a method of use of the inventive device 10, once the proper tension is achieved, the suture ends can be wrapped around cleats on the inserter handle 32 to maintain the desired tension. The surgeon then removes a safety pin from the inserter 12 and rotates the main handle portion 32 clockwise while holding a small inserter knob stationary. This drives the screw 24 inside the implant towards a pinch point, pushing the suture strands 16 into suture cleats 36 in the implant 14 while pinching the suture firmly at the inside bottom of the implant to prevent it from slipping. The handle is rotated until the proximal end of the screw (threaded inside the engagement tube) shears, releasing the inserter from the implant site. An alternate method of releasing the inserter would be to rotate the inserter handle counter-clockwise at the end of the screw's travel, while holding the small knob stationary. At this point, the friction of the suture against the PEEK screw prevents the screw from unscrewing. However, since the handle is rotated counter-clockwise, the inserter would unscrew itself from the end of the PEEK implant screw thus releasing it from the site of implant.

Now with reference to FIG. 12, another embodiment of an inventive suture anchoring device 52 is illustrated. The device 52 is a simple to insert suture anchor which permits adjustment of suture tension prior to deployment, does not change the tension on the suture (and, as a result, the captured tissue) when it is deployed, does not require a knot to secure the suture, and does not require high insertion forces over the entire depth of insertion into the bone socket. The device 52 comprises a distal tip 54, a proximal wedge 56, and an inserter 58, as well as a handle 60. As shown in FIGS. 13A-16, the inserter 58 further comprises an inserter tip 62. A suture eyelet 64 is disposed at a distal end of the distal tip 54. Suture 66 may be loaded onto the device 52, in a manner that will be described below.

Most anchors are supplied pre-loaded with suture passing through an eyelet in the anchor. Such a design is an "anchor first" design, wherein the surgeon drills a hole in a desired location, installs the anchor in the hole, passes one of the free ends of suture through the tissue, and then ties a knot to secure the suture and attached tissue to the anchor. However, the present invention is a "suture first" approach. Again, the surgeon, in a representative procedure performed in accordance with the invention, drills a hole 68 in a desired portion of bone 70 (FIG. 14), in a selected anchoring location. Then, a strand of suture 66 is passed through the tissue (not shown) with the surgeon's choice of suture passing tools. The free suture legs 66a, 66b are then brought out of the patient's body for loading into the suture anchor. FIG. 12 shows the suture anchor components 54, 56 pre-loaded onto the disposable inserter tool 58. The suture anchor comprises two separate parts, the distal tip 54 and the proximal wedge 56, which engage and lock together when deployed within the bone socket 68.

FIG. 13A shows a close-up of the suture anchor components loaded on the inserter tip 62. The suture 66 is shown loaded into the anchor in FIG. 13B. The two free ends 16a, 16b of the suture 66 are passed through the eyelet 64 in the distal tip 54. This step can be aided by the use of a nitinol wire snare or suture snare to pull the ends through the eyelet. The loop shown is the loop which passes through the tissue. The tip of the inserter, with the anchor in place, is then slid down the suture strands into the arthroscopic working space. The distal tip 54 is inserted to the bottom of the drilled hole or socket 68, as shown in FIG. 14. At this point, the surgeon can pull on the free ends 66a, 66b of the suture, which are still outside the patient's body, to add tension and approximate the captured tissue to the anchor location. Once the proper tension is achieved, the suture ends can be wrapped around suture cleats 72 on the handle 60 to maintain the desired tension.

Figure 15:
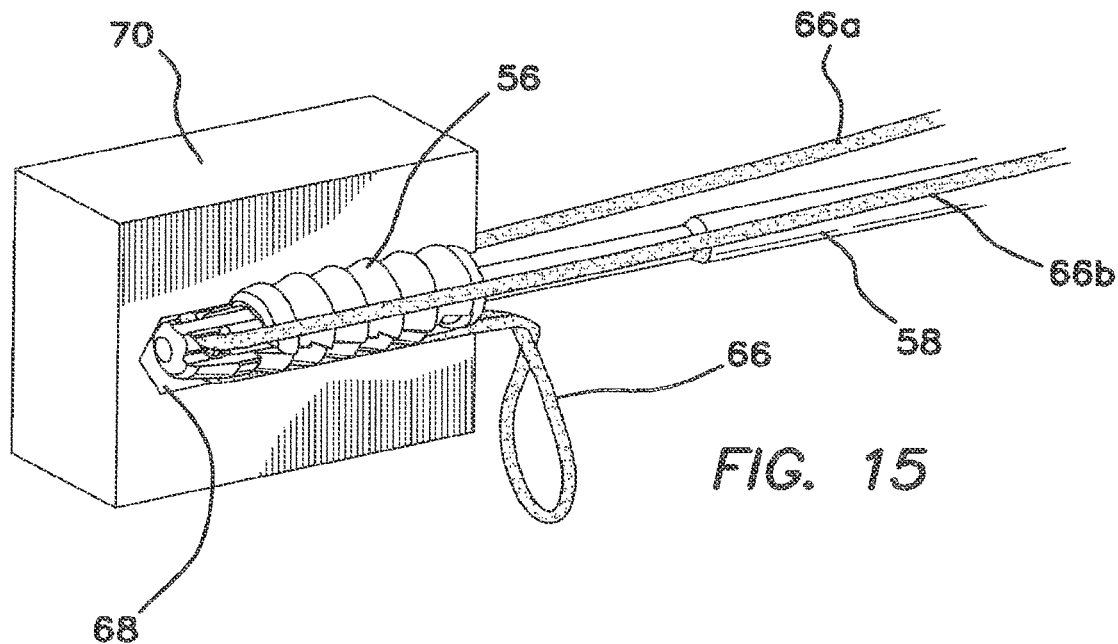
FIG. 15 is an isometric view similar to FIG. 14, wherein the anchor components have been engaged.

Once the proper tension is achieved, the surgeon taps on the end of the inserter handle 60 to push the proximal wedge 56 into the hole 68, as shown in FIG. 15. When the proximal wedge is fully seated, the two anchor components 54, 56 lock together within the socket 68.

Figure 16:
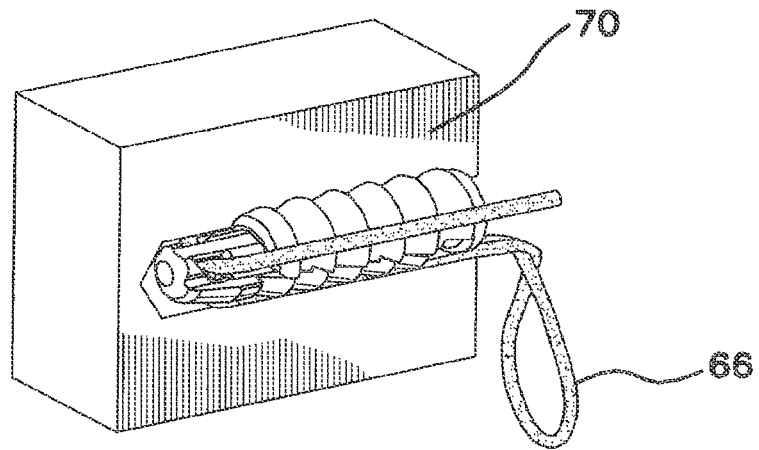
FIG. 16 is an isometric view similar to FIG. 15, wherein the anchor has been fully deployed and the inserter removed.

Finally, as shown in FIG. 16, the inserter tool 58 is removed, and the free ends of the suture are trimmed flush.

Figure 17:
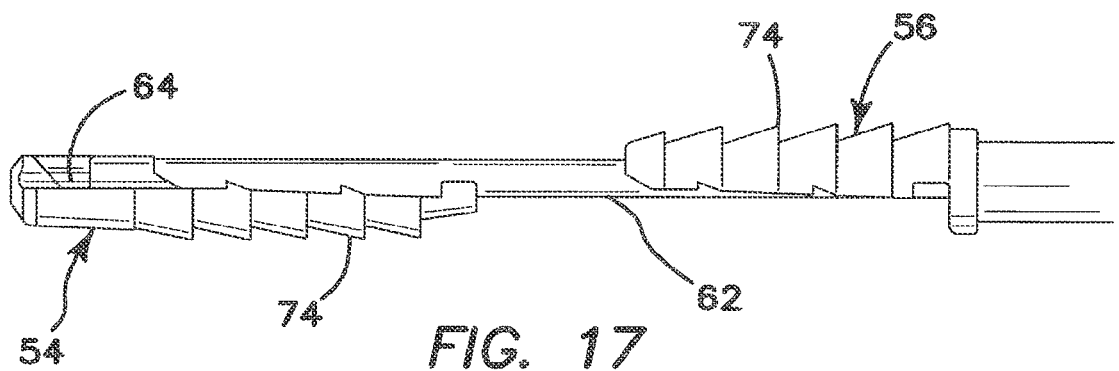
FIG. 17 is an exploded side view of the two components of the anchor of the inserter tip of FIG. 12, prior to deployment with a bone socket.

FIG. 17 illustrates a side view of the two components 54 and 56 of the anchor 52 on the inserter tip 62, prior to deployment within the bone socket 68. The exterior surface of the anchor components comprises barbs 74, although alternative surface features may also be employed for ensuring a solid engagement between the anchor and the interior bony surface of the hole 68.

Figure 18:
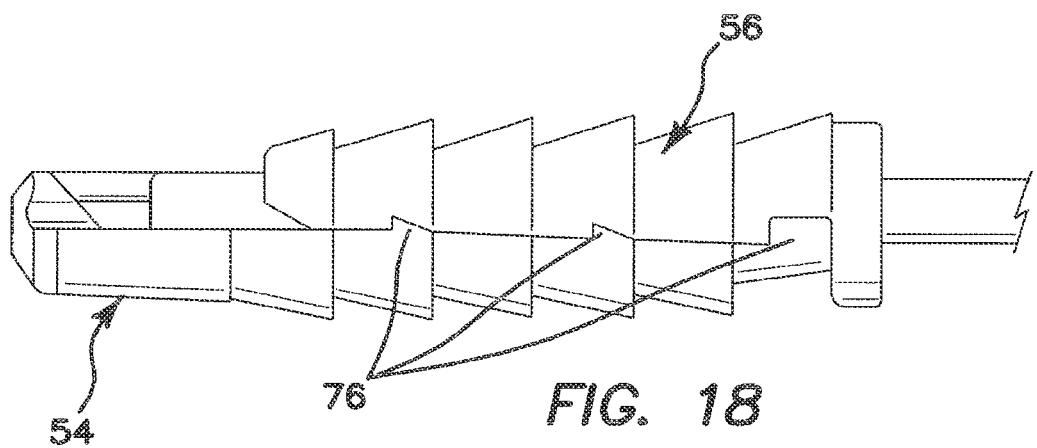
FIG. 18 is a side view similar to FIG. 17 wherein the anchor components of the embodiment of FIG. 12 are fully deployed.

FIG. 18 shows the two components 54, 56 of the anchor in a deployed state. The proximal wedge 56 has been driven against the distal tip 54, locking the two pieces together with three sets of snap features 76. The primary mating surface 78 between the two components 54, 56 is at an angle with respect to the axial orientation of the respective components. This results in the components wedging apart and providing greater interference when fully engaged in the bone hole 68.

Figure 19A:
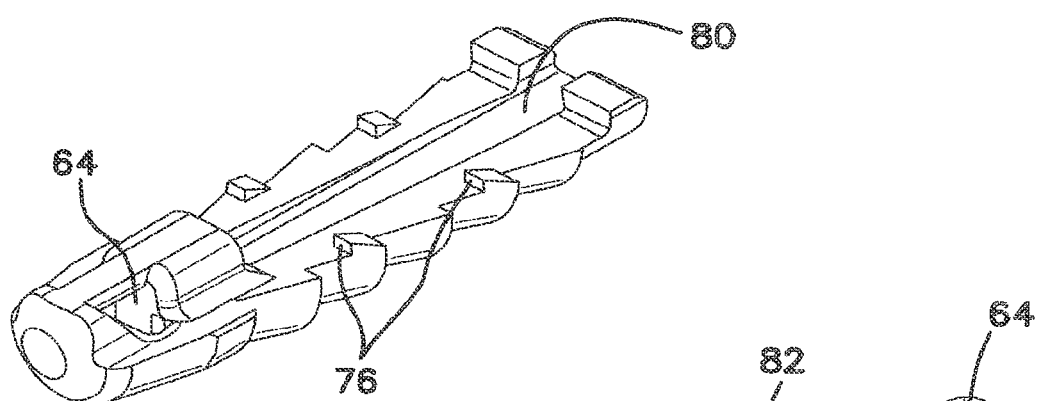
FIG. 19A is an isometric view of one component of the inventive anchor of FIG. 12.
Figure 19B:
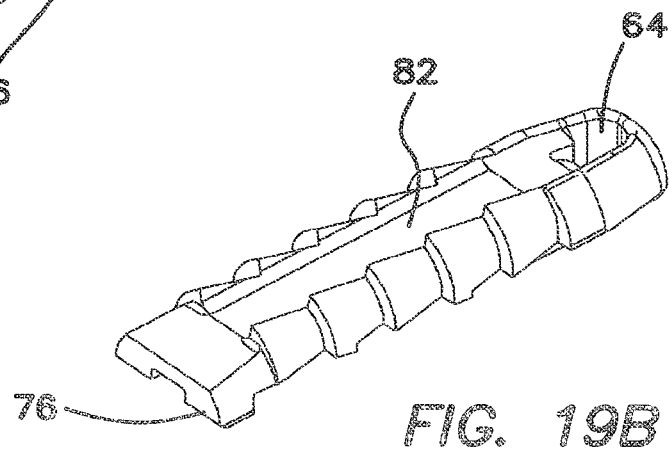
FIG. 19B is a similar view to that of FIG. 19A, illustrating the other major component of the anchor of FIG. 12.

FIGS. 19A and 19B illustrate details of the distal tip 54. The front of the distal tip contains the eyelet 64, through which the suture ends are passed. The eyelet is closed, so that the suture legs 66a and 66b cannot come free of the anchor after they are loaded. The top surface includes a channel 80 to accept the inserter tip 62. In a preferred design, the channel 80 is hourglass-shaped to aid in holding the distal tip 54 onto the matching contour of the inserter tip 62, and to prevent rotation of the components with respect to the inserter. The bottom surface of the distal tip includes a suture channel 82 through which the suture ends pass. This channel 82 allows room for the free suture legs to slide between the anchor and the bone socket when the distal tip is placed at the bottom of the hole 68. When the anchor is deployed, the distal tip is pressed against the side of the bone socket, reducing the size of this channel and compressing the suture between the anchor and the bone.

Figure 20A:
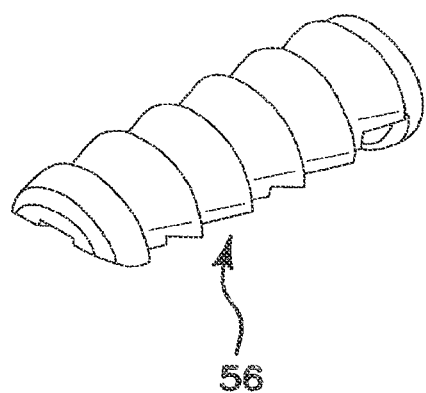
FIG. 20A is a top isometric view of the proximal wedge of the embodiment of FIGS. 12-19B.
Figure 20B:
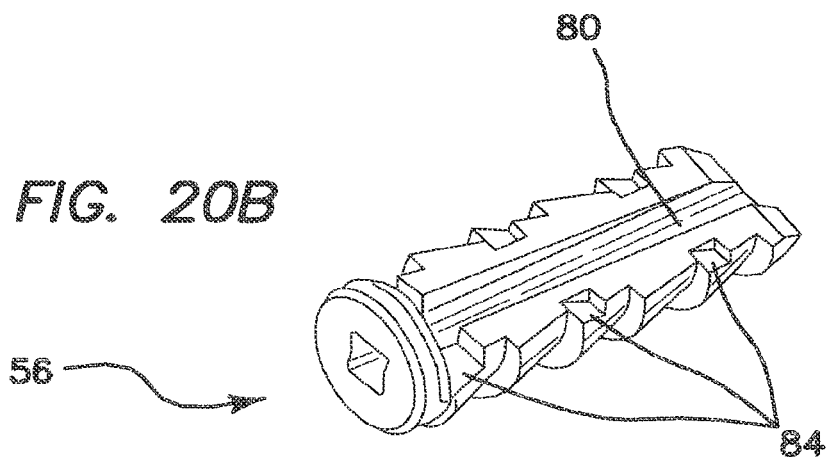
FIG. 20B is a bottom isometric view of the proximal wedge of FIG. 20A.

Two views of the proximal wedge 56 are shown in FIGS. 20A and 20B. This component contains; the same hourglass-shaped channel 80 to hold the part onto the inserter tip 62 and prevent rotation. There are also corresponding snap feature notches which engage with the snap features 76 on the distal tip to lock the two parts together when deployed.

Figure 21:
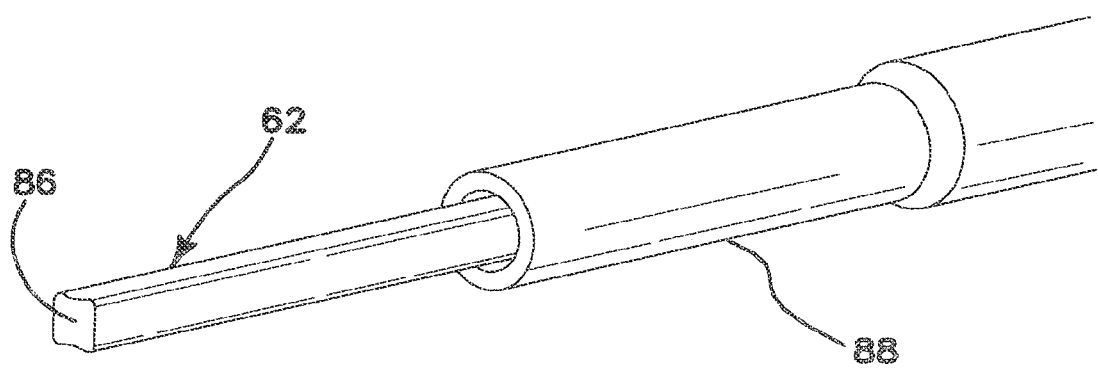
FIG. 21 is an isometric view of the inserter distal end of the embodiment of FIGS. 12-20B.

The distal end of the inserter 58, illustrated in FIG. 21, includes two components to deploy the anchor 10. The inserter tip 62 has an hourglass profile 86. The hourglass shape helps to secure and prevent rotation of the anchor components on the tip. Just proximal to the tip is an insertion sleeve 88. When the end of the inserter is tapped with a mallet, the insertion sleeve 88 moves distally to drive the proximal wedge 56 into the hole 68 and engage with the distal tip 54.

The handle 60 of the inserter is shown in FIG. 22. The distal end of the handle includes a set of suture cleats 72. After a proper suture tension has been achieved, the suture may be wrapped around the cleats 72 to secure them and prevent further movement. The inserter handle 60 is fixed relative to the hourglass-shaped inserter tip 62. At the proximal end of the handle 60 is a knob 90. The knob is fixed relative to the insertion sleeve 88. When the knob 90 is tapped with a hammer, it drives the insertion sleeve 88 and the proximal wedge 56 forwardly with respect to the handle, which the surgeon is holding, and the distal tip 54. The knob 90 moves flush with the end of the handle when the two anchor components 54, 56 are fully engaged.

There are several variations from the above described embodiment of FIGS. 12-22 which may be incorporated, if desired. For example, with respect to the implant, the external holding features of the anchor components (shown in the depicted embodiment as the circumferential barbs 74) could be a number of different shapes, depending upon desired performance and location of the anchor. The circumferential features may be ridges, with equal angles on both the leading and trailing edges, especially on the distal tip 54. This could aid in preventing the distal tip from moving in either direction, distally or proximally, after deployment. The barbs may be interrupted to reduce insertion forces in hard bone or to encourage tissue ingrowth after insertion.

In addition, the blind hole in the distal tip could include features which aid in holding the distal tip onto the inserter tip. Three of these potential variations are discussed below.

FIGS. 23A and 23B show a variation of the inserter tip 62 and implant which offers improved retention of the distal tip on the inserter tip. For this variation, a transverse hole 92 has been added to the distal tip, which intersects the hourglass-shaped blind hole. The inserter tip shaft has been modified to include a central hole down the center with a ramp feature 94 at the distal end of the part. A wire 96 is located within this central hole. This position is the "unlocked" position, and the inserter tip can be pulled to the right and out of the distal tip. When the wire is slid distally (to the left) within the inserter tip, it is diverted by the ramp feature and forced to extend proud of the surface of the inserter tip, slightly into the transverse hole in the distal tip (FIG. 23B). This is the "locked" position, which does not allow the inserter tip to be pulled to the right and out of the distal tip.

Figure 25:
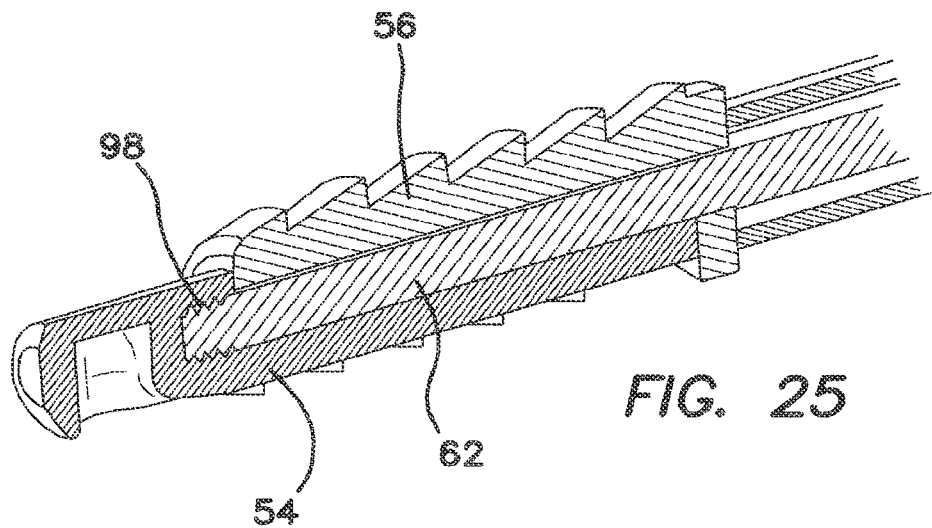
FIG. 25 is an isometric cross-sectional view of the inserter tip of FIG. 24.

Another variation which serves the same purpose is shown in FIGS. 24 and 25. FIG. 24 shows a modification to the end of the inserter tip. In this design, the tip has a round cross-section where the distal tip is held. Just proximal to the round section, the inserter tip has the same hourglass shape as shown in the afore described embodiments.

FIG. 25 shows a cross-section of the inserter tip, distal tip, and proximal wedge. As can be seen in this view, the most distal end of the inserter tip is threaded over a small portion of its length. The hole in the distal tip into which the inserter tip fits includes a mating threaded portion 98. This threaded portion serves to secure the distal tip to the end of the inserter tip. When the proximal wedge is deployed, it is pushed beyond the hourglass-shaped portion of the inserter tip. Once in the position shown, the inserter tip can be rotated to unscrew the threads from the distal tip and removed.

Figure 26A:
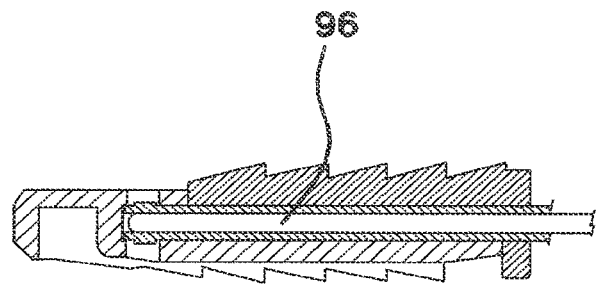
FIG. 26A is a side cross-sectional view of yet another modified embodiment of the inserter tip of FIGS. 12-21, wherein the flex arm is in a locked position.
Figure 26B:
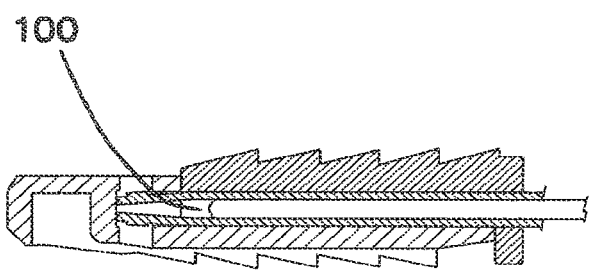
FIG. 26B is view similar to FIG. 26A, wherein the flex arm is in an unlocked position.

Yet another variation of the inserter tip is shown in FIGS. 26A and 26B. The version illustrated requires two transverse holes in the distal tip which intersect the hourglass-shaped blind hole. This distal end of the inserter tip includes a central hole through which a wire can pass, a thin slot 100 cut through the end, and two small bumps. As shown in FIG. 26A, the wire is positioned at the end of the inserter tip. In this position, the distal tip cannot be pulled to the right and out of the distal tip. When the wire is pulled to the right (FIG. 26B), the end of the inserter tip is allowed to flex at the thin slot 100, which flexes the bumps out of the transverse holes and allows the inserter tip to pull out of the distal tip.

Figure 27:
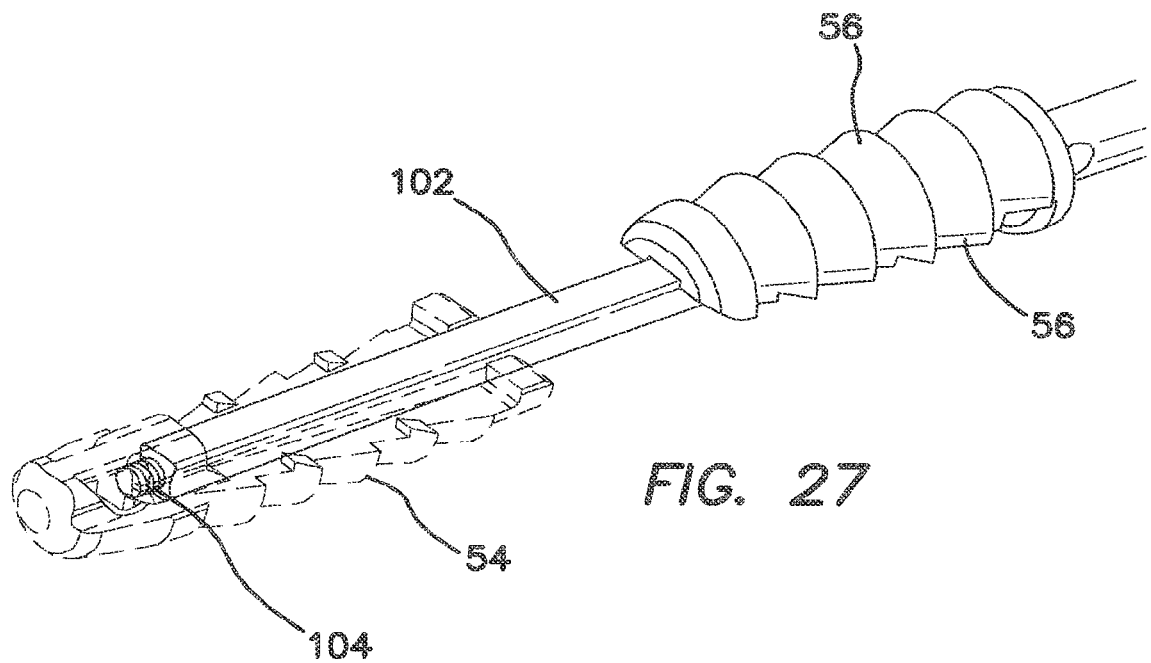
FIG. 27 is an isometric view of still another embodiment of the inserter tip of FIGS. 12-21.
Figure 28:
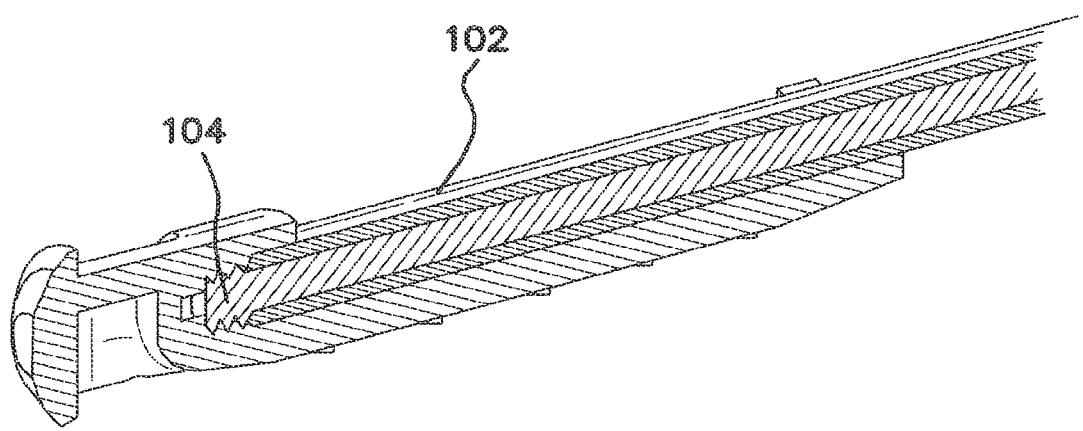
FIG. 28 is a cross-sectional view of the distal portion of the embodiment of FIG. 27.

FIGS. 27 and 28 illustrate another variation of a method of locking the distal tip onto the end of the inserter tip. In this embodiment, the external, distal end of the inserter tip comprises the hourglass profile of prior embodiments. However, the inserter tip is cannulated, through which an inner wire passes. The inner wire has a threaded portion 104 which extends beyond the end of the inserter tip. This threaded portion threads into an internally threaded hole in the distal tip. FIG. 28 shows, specifically, a detailed cross-section of the distal tip, threaded inner wire, and inserter tip. The threads of the inner wire and distal tip engage to secure the distal tip on the end of the assembly. To unlock, the inner wire is rotated to disengage the threads, and the inserter tip can be removed. The threaded portion of the inner wire can have threads which are the same diameter as the inner wire, or, alternative, can have either a smaller or a larger diameter.

Figure 29:
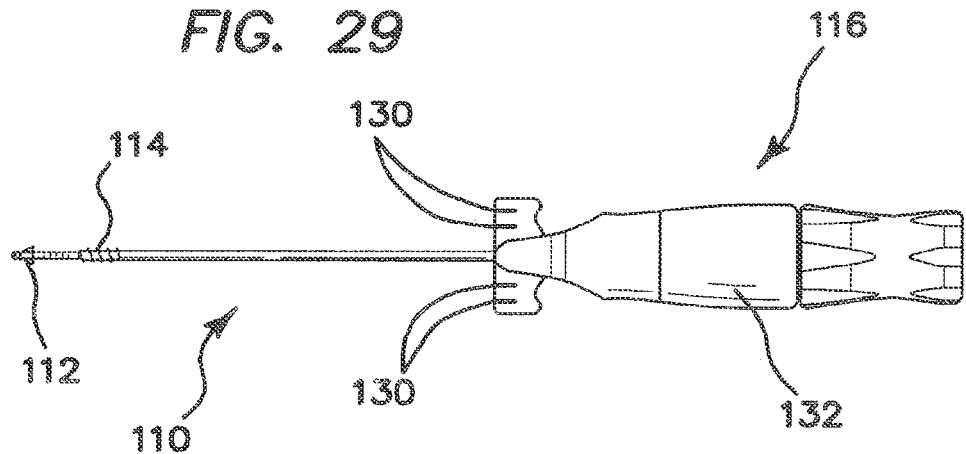
FIG. 29 is a plan view of another, presently preferred, embodiment of an inserter for installing a suture anchor.

In FIG. 29, there is shown another embodiment of a suture anchoring device 110. The suture anchor comprises two components, namely, a distal tip or implant 112, and a proximal screw 114. Components 112 and 114 are pre-loaded onto a disposable inserter tool 116.

The procedure for installing the suture anchor of the present invention is similar to the procedure many surgeons are familiar with for installing existing suture anchors. Most anchors are supplied pre-loaded with suture passing through an eyelet in the anchor. Such designs are known as "anchor first designs". The surgeon drills a hole in the desired location, installs the anchor into the hole, passes one or both of the free ends of suture through the tissue, and then ties a knot to secure the suture and attached tissue to the anchor.

In contrast, the current invention is a "suture first" design. Again, the surgeon drills a hole in the bone at the desired anchoring location. For the next step, a strand of suture is passed through the desired tissue with the surgeon's choice of suture passing devices. The free suture legs are then brought outside the patient's body for loading into the suture anchor.

Figure 30:
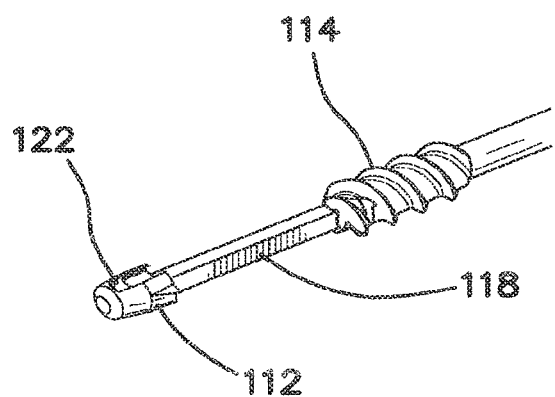
FIG. 30 is an isometric view of components of the suture anchor loaded on the distal tip of the inserter of FIG. 29.
Figure 31:
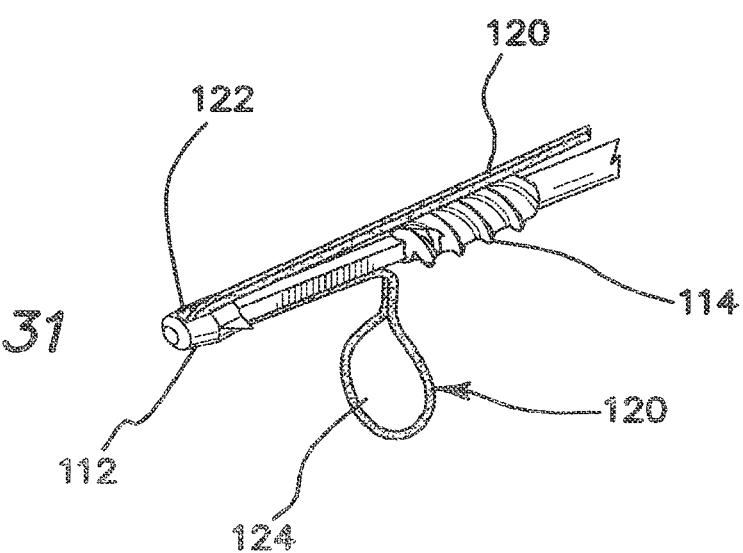
FIG. 31 is an isometric view similar to FIG. 30, showing a length of suture loaded onto the suture anchor.

FIG. 30 shows a close-up view of the suture anchor components 112 and 114 loaded on an insert tip 118. Suture 120 is shown loaded into the anchor in FIG. 31. The two free ends of the suture 120 are passed through an eyelet 122 in the distal tip 112. This step of threading the suture 120 through the eyelet 122 can be aided by use of a nitinol wire snare or suture snare to pull the ends through the eyelet. The suture loop 124 shown in FIG. 31 is the loop which is passed through the tissue to be approximated (not shown).

Figure 32:
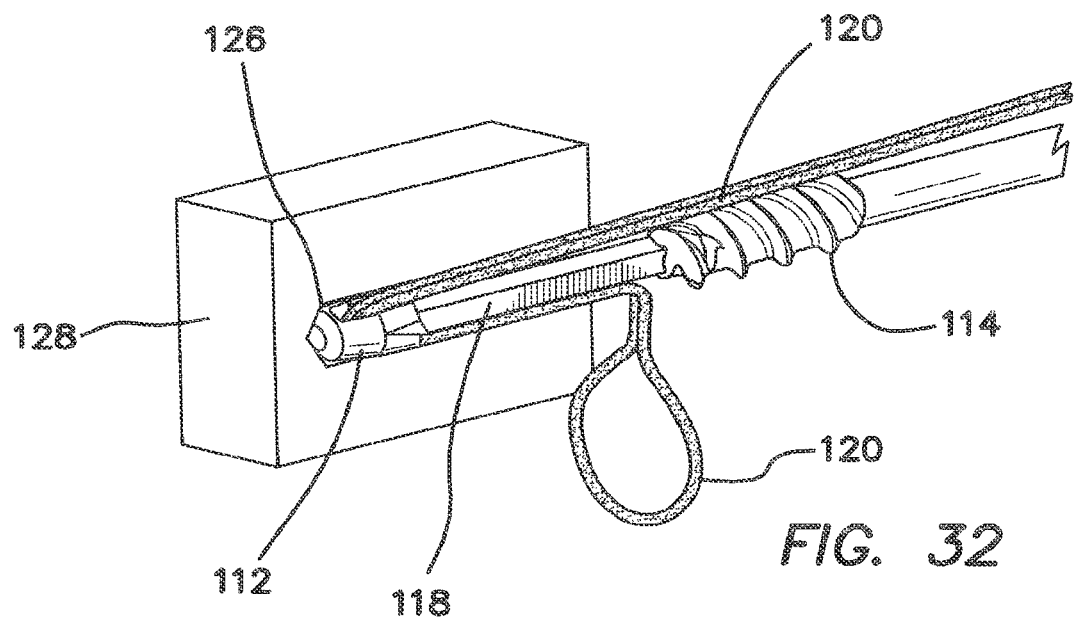
FIG. 32 is an isometric view showing the distal tip of the inserter of FIG. 29 after it has been slid along the suture strands into an arthroscopic working space within a patient.

Now with reference to FIG. 32, the tip 118 of the inserter, with the anchor in place, is then slid down the suture strands 120 into the arthroscopic working space. The distal tip 112 is inserted to the bottom of a drilled hole or socket 126 in the bone 128, as shown in FIG. 32. At this juncture, the surgeon may pull on the free ends of the suture 120, which are still outside the body, to add tension and approximate the captured tissue to the anchor location. Once the proper tension is achieved, the suture ends can be wrapped around suture cleats 130 on handle 132 (FIG. 29) to maintain the desired tension.

Figure 33:
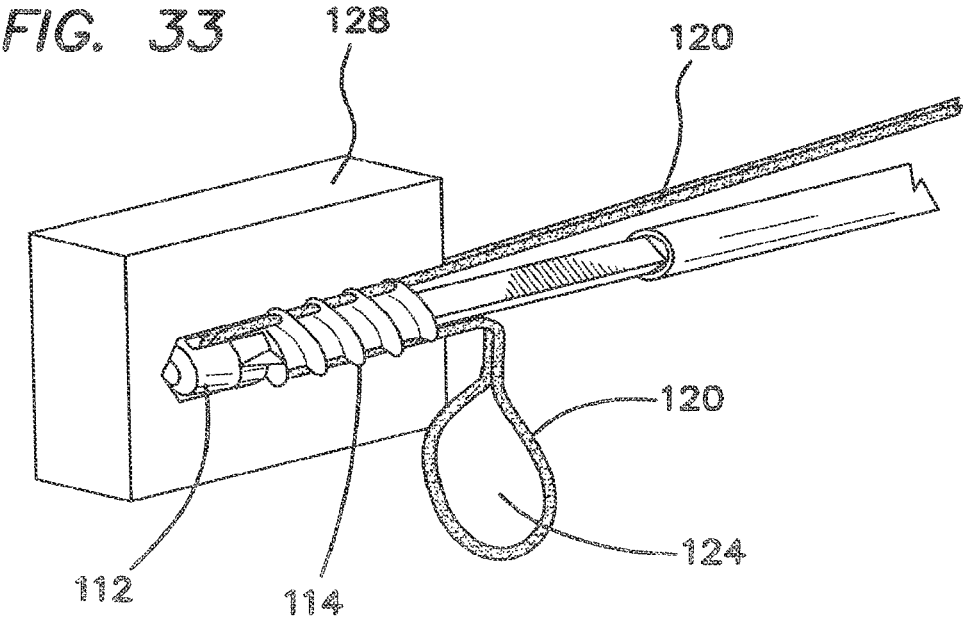
FIG. 33 is an isometric view similar to FIG. 32, showing the device after the suture has been tensioned and the proximal screw has been advanced into the working space.

Once the proper tension is achieved, the surgeon advances the proximal screw 114 to the socket 126, in a manner to be discussed in more detail below, and rotates the end of the inserter handle to screw the proximal screw 114 into the socket 126, as shown in FIG. 33.

Figure 34:
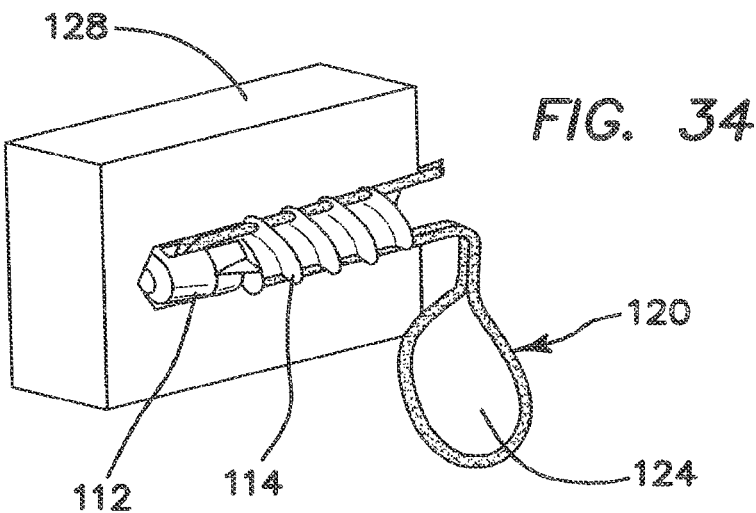
FIG. 34 is an isometric view similar to FIG. 33, showing the suture anchor in place within the working space, with the inserter tool removed and the free ends of the suture trimmed flush.

Finally, as shown in FIG. 34, the inserter tool 116 is removed, and the free ends of the suture 120 are trimmed flush to complete the procedure.

Figure 35:
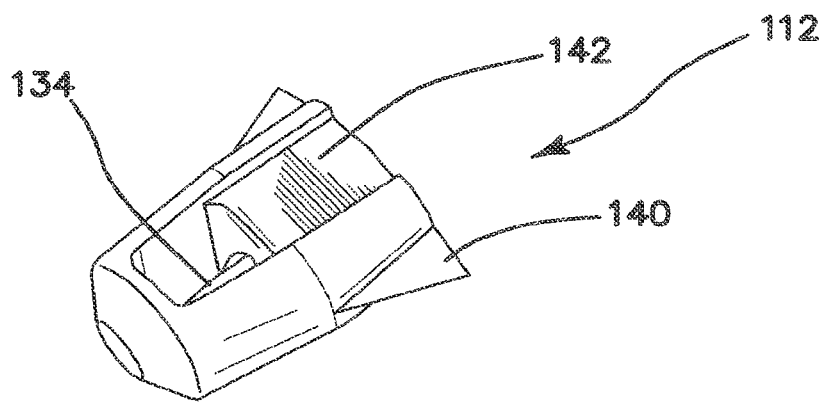
FIG. 35 is an isometric view of the distal tip of the inserter of FIG. 29, shown in isolation.
Figure 36:
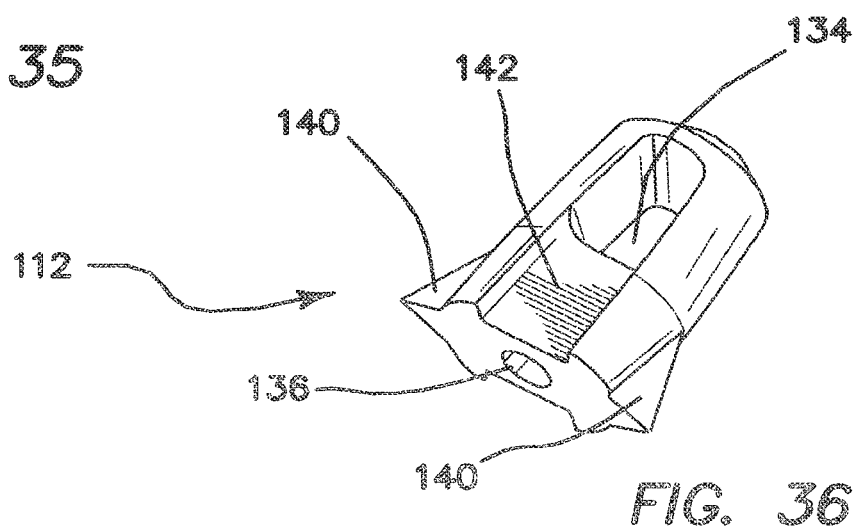
FIG. 36 is an isometric view similar to FIG. 35, showing the distal tip from the opposing side.
Figure 39:
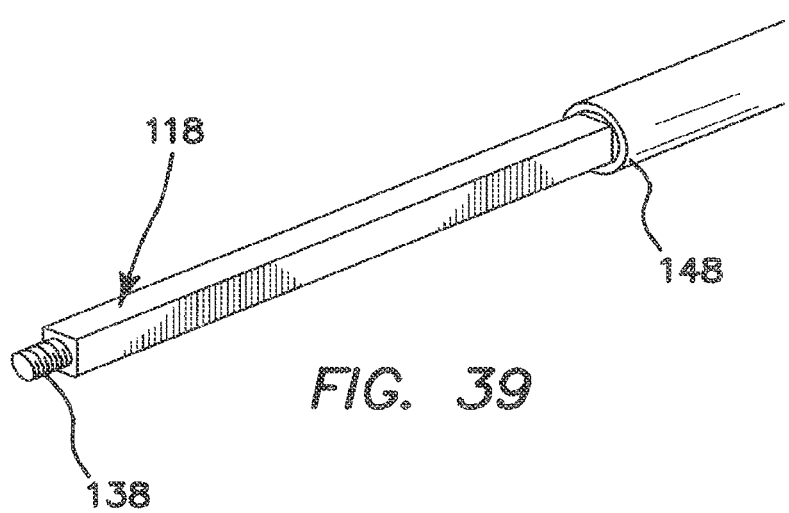
FIG. 39 is an isometric view of the inserter tip of the present invention.

Now, with reference to FIGS. 35 and 36, additional constructional details of the distal tip 112 of the anchor are illustrated. The distal tip 112 comprises a transverse hole, or eyelet 134, through which the suture ends are passed. The eyelet is closed so that the suture legs cannot come free of the anchor after they are loaded. The rear surface of the distal tip 112 includes a threaded hole 136 (FIG. 36) for accepting the threaded tip 138 of the inserter tip 118 (FIG. 39). In a preferred design, the threaded hole 136 has a left-hand thread, so as the inserter tip 118 is rotated clockwise to drive the proximal screw 114 into the bone socket 126, the distal tip 112 is unscrewed from the inserter tip 118.

The distal tip 112 also includes features, illustrated in FIGS. 35 and 36 as triangular ribs 140, to prevent the tip from rotating in the socket 126 as the inserter tip 118 is rotated. If the distal tip 112 rotates when the inserter tip 118 turns, it might not unscrew from the inserter tip and it could wind the suture 120 within the socket. These anti-rotation features may take many alternative forms, such as ribs of other cross-sections, posts, thicker walls on the sides of the distal tip 112, etc. The top and bottom features of the distal tip 112 include a suture channel 142 where the suture strands lie. These channels 142 allow room for the suture strands to slide (to approximate the tissue to the socket) between the anchor and the bone socket when the distal tip is placed at the bottom of the socket.

Figure 37:
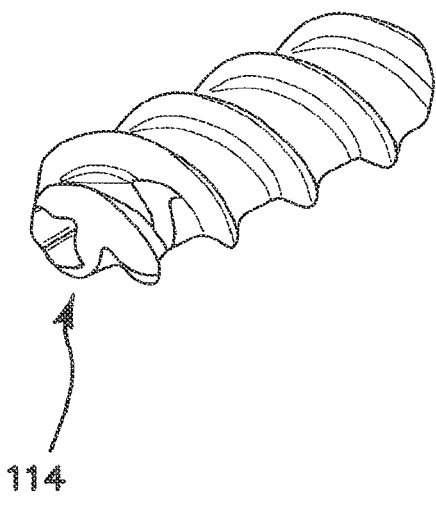
FIG. 37 is an isometric view of the proximal screw of the present invention, shown in isolation.
Figure 38:
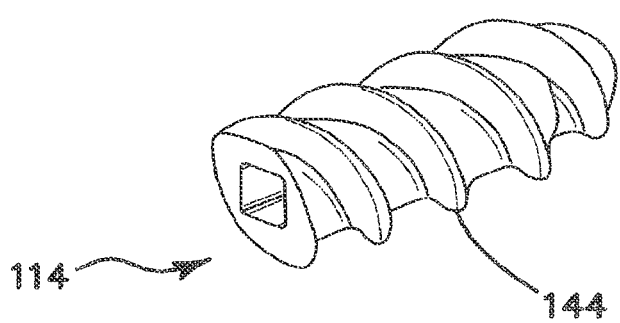
FIG. 38 is an isometric view similar to FIG. 37, from an opposing side.

Two views of the proximal screw 114 are shown in FIGS. 37 and 38. The screw has a thread profile 144 which is designed to optimize the holding force within the bone socket 126, securely compresses the suture 120 against the walls of the bone socket, and does not grab or damage the suture as it is inserted. The screw thread is also a double-start thread to reduce the number of turns required to fully insert the anchor. The proximal screw 114 has a central bore 146, which is shown in the preferred design as a square cross-section. The profile of this bore could alternatively be any shape which allows torque to be transmitted from the inserter tip 118 to the proximal screw 114—rectangular, triangular, hexagonal, etc.

The inserter tip 118 is shown in FIG. 39. Three features of this inserter tip assist in deploying the anchor. The inserter tip 118 has a square profile which matches the internal bore 146 of the proximal screw 114, so that the proximal screw 114 slides over the inserter tip, as illustrated. The square profile transmits torque from the driver to the proximal screw. The distal end of the inserter tip 118 includes the previously described threaded tip 138, for engaging with the internal threaded hole 136 on the distal tip 112. The threads serve to hold the distal tip 112 on the inserter tip 118, and to unscrew the distal tip as the proximal screw is rotated and inserted, as described above. Just proximal to the inserter tip 118 is an insertion sleeve 148. When the end of the inserter is pushed forward, the insertion sleeve 148 moves distally to drive the proximal screw to the entrance of the bone socket 126 where the threads on the proximal screw 114 can engage the hole when the screw is rotated.

Figure 40:
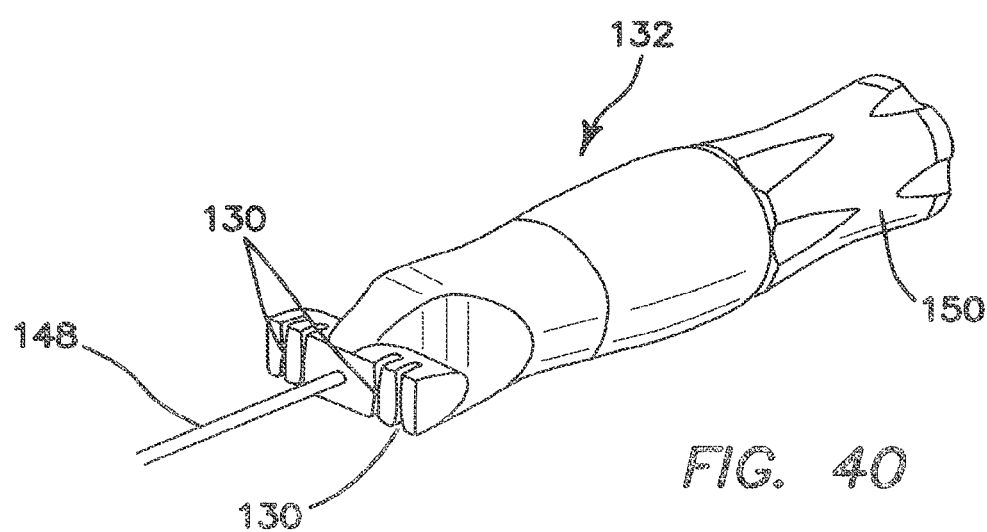
FIG. 40 is an isometric view of the inserter handle of the present invention.

The handle 132 of the suture anchoring device 110 is shown in FIG. 40. As noted previously, a distal end of the handle 132 comprises a set of suture cleats 130. After the proper suture tension has been achieved, as discussed above, the suture may be wrapped around the cleats to secure them and maintain tension on the suture strands. At the proximal end of the handle 132 is a knob 150. When the knob is pushed forward, it drives the insertion sleeve 148 and proximal screw 114 forward with respect to the handle, which the surgeon is holding. The knob moves flush with the end of the handle when the proximal screw 114 is seated on the entrance of the bone socket 126. The knob is then rotated clockwise, which rotates the inserter tip 118 and the proximal screw 114, driving the screw 114 into the hole and securing the suture 120 and the distal tip 112.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. An anchoring system for securing suture to bone, comprising:
    an implant comprising a distal tip having a suture securing portion and having external surface features for securing the implant within surrounding bone;
    a proximal member which is movable distally to engage the distal tip and to fix the suture in place within the implant and relative to the bone; and
    an inserter which is removably connectable to a proximal end of the implant, the inserter including an outer inserter shaft and an inner engagement tube, the engagement tube being rotatable relative to the inserter shaft to move the engagement tube distally within the inserter shaft, thereby moving the proximal member distally to fix the suture within the implant.

2. The anchoring system of claim 1, wherein the proximal member comprises a screw member.

3. The anchoring system of claim 2, wherein the implant includes a threaded internal surface structured to engage with a threaded external surface of the screw member.

4. The anchoring system of claim 1, wherein the engagement tube is structured to engage with a proximal end of the proximal member.

5. The anchoring system of claim 1, wherein the implant includes an external surface, and wherein the external surface includes a suture channel for permitting the suture to slide along the external surface for tissue tensioning.

6. The anchoring system of claim 1, wherein the inserter includes a handle at a proximal end thereof.

7. The anchoring system of claim 6, wherein the handle includes a rotatable knob.

8. The anchoring system of claim 7, wherein rotation of the knob relative to the handle causes a corresponding rotation of the engagement tube relative to the inserter shaft.

9. The anchoring system of claim 1, wherein the suture securing portion structured to enable a suture to pass through the implant from one side to the opposite side.

10. An anchoring system for securing suture to bone, comprising:
    an implant including an external surface and a distal tip, the distal tip including a suture securing portion structured to enable a suture to pass through the suture securing portion from one side to the opposite side;
    a proximal member engageable with the implant via a threaded connection, the proximal member configured to be driven distally to engage the distal tip and to fix the suture in place within the implant; and
    an inserter extending along a longitudinal axis from a proximal end to a distal end and including an inserter shaft and an engagement member rotatable relative to the inserter shaft, wherein a distal end of the engagement member is engageable with a proximal end of the proximal member, and wherein rotation of the engagement member about the longitudinal axis drives the engagement member distally, thereby driving the proximal member distally to fix the suture within the implant.

11. The anchoring system of claim 10, wherein the external surface of the implant includes a plurality of external surface features for securing the implant within surrounding bone.

12. The anchoring system of claim 10, wherein the external surface of the implant includes a suture channel extending through at least some of the external surface features.

13. The anchoring system of claim 10, wherein the engagement member is at least partially disposed within a lumen of the inserter shaft.

14. The anchoring system of claim 10, wherein the distal tip of the implant is tapered.

15. An anchoring system for securing suture to bone, comprising:
    a distal member including an external surface and a suture securing portion structured to enable a suture to pass through the suture securing portion from one side to the opposite side, the external surface including one or more external surface features for securing the distal member within surrounding bone;
    a proximal member configured to be at least partially received within a cavity of the distal member, the proximal member being movable distally to fix the suture in place within the distal member and relative to the bone; and
    an inserter extending along a longitudinal axis from a proximal end to a distal end, the distal end of the inserter configured to removably engage with a proximal end of the distal member, the inserter including an inserter shaft and an engagement tube rotatable relative to the inserter shaft, wherein rotation of the engagement tube about the longitudinal axis causes the engagement tube to move distally, thereby moving the proximal member distally to fix the suture within the distal member.

16. The anchoring system of claim 15, wherein the distal member includes a suture channel for permitting the suture to slide along the external surface for tissue tensioning.

17. The anchoring system of claim 15, wherein the distal member engages with the proximal member via a threaded connection.

18. The anchoring system of claim 15, wherein the one or more external surface features comprise frustoconical surfaces.

19. The anchoring system of claim 15, wherein the one or more external surface features comprise barbs.

20. The anchoring system of claim 15, wherein the distal member includes a tapered distal tip.

\* \* \* \* \*